United States Patent
Al-Otaibi et al.

(10) Patent No.: US 10,444,218 B2
(45) Date of Patent: Oct. 15, 2019

(54) MULTIPLE FUNCTION DUAL CORE FLOODING APPARATUS AND METHODS

(71) Applicant: Saudi Arabian Oil Company, Dhahran (SA)

(72) Inventors: Fawaz Al-Otaibi, Dhahran (SA); Xianmin Zhou, Dhahran (SA); Ahmed A. Eidan, Dhahran (SA); Sunil Kokal, Dhahran (SA); Almohannad A. Alhashboul, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 224 days.

(21) Appl. No.: 15/452,949

(22) Filed: Mar. 8, 2017

(65) Prior Publication Data
US 2018/0045704 A1    Feb. 15, 2018

Related U.S. Application Data

(60) Provisional application No. 62/372,489, filed on Aug. 9, 2016.

(51) Int. Cl.
*E21B 49/00* (2006.01)
*G01N 33/24* (2006.01)
(Continued)

(52) U.S. Cl.
CPC ............ *G01N 33/24* (2013.01); *G01N 9/32* (2013.01); *G01N 11/04* (2013.01); *E21B 25/00* (2013.01); *E21B 49/02* (2013.01)

(58) Field of Classification Search
CPC .......... G01N 33/24; G01N 9/32; G01N 11/04; E21B 25/00; E21B 49/02; F17D 3/00
See application file for complete search history.

(56) References Cited

U.S. PATENT DOCUMENTS 3,839,899 A * 10/1974 McMillen ............... G01B 13/02
33/501.03
4,304,122 A * 12/1981 Tentor ............... G01N 15/0826
73/152.07
(Continued)

OTHER PUBLICATIONS

Xianmin Zhou et al: "Novel Insights into IOR/EOR by Seawater and Supercritical CO2 Miscible Flooding Using Dual Carbonate Cores at Reservoir Conditions", Saudi Aramco Journal of Technology, Jun. 1, 2015 (Jun. 1, 2015), pp. 1-11, XP055416146.*
(Continued)

*Primary Examiner* — Harshad R Patel
*Assistant Examiner* — Nigel H Plumb
(74) *Attorney, Agent, or Firm* — Bracewell LLP; Constance G. Rhebergen; Brian H. Tompkins

(57) ABSTRACT

A dual core flooding apparatus is disclosed. The dual core flooding apparatus includes at least two core holders each configured to contain a core plug. The dual core flooding apparatus includes a fluids delivery system configured to inject one or more fluids into the core holders and core plugs. The dual core flooding apparatus includes an image capture system, a density and viscosity measurement system, and at least two oil/water separators. The dual core flooding apparatus also includes at least two back pressure regulators configured to maintain a pore pressure in the core plugs and an automated confining pressure system configured to maintain a confining pressure in each core holder. The dual core flooding apparatus further includes a data acquisition system, differential pressure measurement systems, and effluent measurement systems.

16 Claims, 24 Drawing Sheets

(51) Int. Cl.
  *G01N 9/32* (2006.01)
  *G01N 11/04* (2006.01)
  *E21B 25/00* (2006.01)
  *E21B 49/02* (2006.01)

(56) References Cited

U.S. PATENT DOCUMENTS

| | | | | |
|---|---|---|---|---|
| 4,506,542 A * | 3/1985 | Rose | G01N 15/0826 | 73/38 |
| 4,543,821 A * | 10/1985 | Davis, Jr. | G01N 15/0826 | 324/376 |
| 4,586,376 A * | 5/1986 | Outmans | E21B 49/00 | 73/38 |
| 4,649,737 A * | 3/1987 | Jones | G01N 15/08 | 73/38 |
| 4,868,751 A * | 9/1989 | Dogru | G01N 15/08 | 702/12 |
| 4,884,438 A * | 12/1989 | Jones | G01N 15/0826 | 73/152.11 |
| 5,133,207 A * | 7/1992 | Wilson | G01N 15/0826 | 73/38 |
| 5,209,104 A * | 5/1993 | Collins | G01N 33/241 | 324/376 |
| 5,261,267 A * | 11/1993 | Kamath | G01N 15/0826 | 73/38 |
| 5,637,796 A * | 6/1997 | Deruyter | G01N 15/0806 | 73/152.09 |
| 5,783,760 A * | 7/1998 | Haines | G01N 15/082 | 73/865.6 |
| 7,805,982 B2 * | 10/2010 | Hilab | E21B 25/005 | 73/38 |
| 8,356,510 B2 * | 1/2013 | Coenen | G01N 33/241 | 73/38 |
| 8,683,858 B2 | 4/2014 | Piri | | |
| 2012/0211089 A1 * | 8/2012 | Piri | C09K 8/58 | 137/14 |
| 2015/0219789 A1 * | 8/2015 | Pairoys | G01V 9/00 | 73/118.04 |

OTHER PUBLICATIONS

Zuo: "An Experimental Study of CO2 Exsolution and Relative Permeability Measurements During CO2 Saturated Water Depressurization", A report Submitted to the Department of Energy Resources Engineering of Stanford University in Partial Fulfillment of the Requirements for the Degree of Master of Science, Jun. 1, 2011.*

International Search Report and Written Opinion for International Application No. PCT/US2016/045821; dated Nov. 3, 2017; pp. 1-14.

Sun et al. "Laboratory Core Flooding Experimental Systems for C02 Geosequestration: An Updated Review Over the Past Decade", Journal of Rock Mechanics and Geotechnical Engineering, vol. 8, Feb. 1, 2016; pp. 113-126.

Zhou et al: "Novel Insights into IOR/EOR by Seawater and Supercritical C02 Miscible Flooding Using Dual Carbonate Cores at Reservoir Conditions"; Saudi Aramco Journal of Technology, Jun. 1, 2015; pp. 1-11.

Zuo et al. "An Experimental Study of C02 Exsolution and Relative Permeability Measurements During C02 Saturated Water Depressurization" A Report Submitted to the Department of Energy Resources Engineering of Stanford University in Partial Fulfillment of.

API "Recommended Practices for Core Analysis" American Petroleum Institute; Recommended Practice 40; Second Edition, Feb. 1998; pp. 1-235.

Coretest Systems, Inc.; "MEP-704 Modular Electrical Properties and Capillary Displacement System" accessible as of Jan. 11, 2016 from the website: http://www.coretest.com/product_detail.php?p_id=103; pp. 1-2.

Coretest Systems, Inc.; "SFS-32 Two-Phase Sonic Fluid Separator" accessible as of Jan. 11, 2016 at the website: http://www.coretest.com/sonic-fluid-separator.html; 1 p.

Netl "Carbon Dioxide Enhanced Oil Recovery—Untapped Domestic Energy Supply and Long Term Carbon Storage Solution" National Energy Technology Laboratory, U.S. Department of Energy; Mar. 2010; pp. 1-32.

Perrin, Jean-Christophe, et al.; "Core- and pore-scale experimental study of relative permability properties of CO2 and brine in reservoir rocks" Department of Energy Resources Engineering, Stanford University; 2008; pp. 1-18.

* cited by examiner

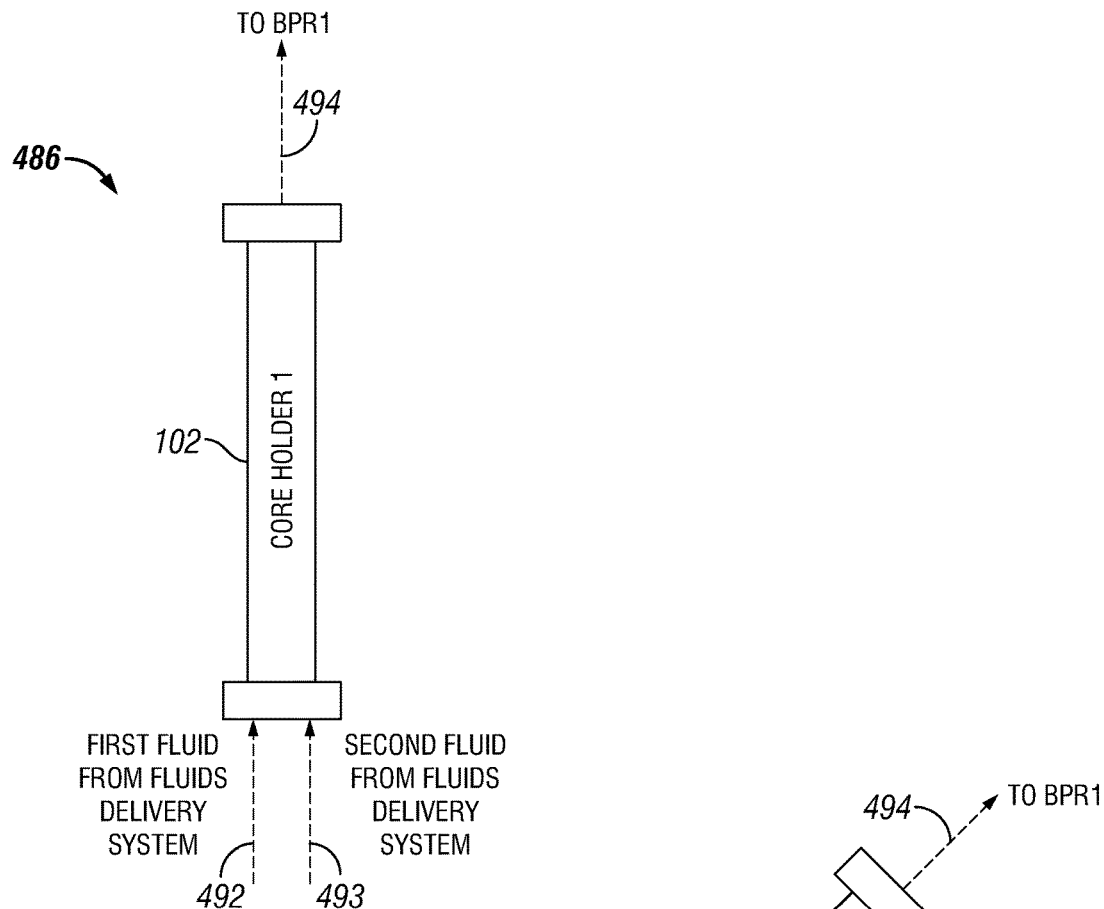

MULTIPLE FUNCTION DUAL CORE FLOODING APPARATUS AND METHODS

CROSS-REFERENCE TO RELATED APPLICATIONS

This application claims priority from U.S. Provisional Application No. 62/372,489 filed Aug. 9, 2016, and titled "MULTIPLE FUNCTION DUAL CORE FLOODING APPARATUS AND METHODS." For purposes of United States patent practice, this application incorporates the contents of the Provisional Application by reference in its entirety.

BACKGROUND

Field of the Disclosure

Embodiments of the disclosure generally relate to apparatus and methods for the evaluation of flow characteristics and behaviors of fluids, such as crude oil, seawater, supercritical $CO_2$/gas $CO_2$, and chemical solutions, in rock samples obtained from reservoirs (for example, sandstone or carbonate reservoirs).

Description of the Related Art

During rock coring in development and exploration of a hydrocarbon reservoir to produce hydrocarbons such as oil and gas, rock core samples of subsurface material are collected. The process of obtaining these samples, referred to as "cores," "core samples," or "core plugs," produces a corebore hole that is formed into and defined by and traverses the subsurface (that is, the rock or other material beneath the surface). A core plug is the extracted subsurface material (such as rock or stone) obtained from the subsurface through the newly formed corebore. In some instances, core plugs can be taken from and compose a portion of a reservoir or formation.

Following extraction, core plugs may transported to a laboratory or other location, and analyzed to evaluate characteristics of the hydrocarbon reservoir or subsurface. For example, core analysis may include an analysis of rock properties of the core plug, permeability of the core plug, and flooding performance. A typical core analysis system includes a single stationary core holder that holds one core plug for performing tests on the core plug. Such a system may only provide for one orientation of the single stationary core holder and for limited flooding tests with a single fluid. Additionally, such systems may be unable to accurately reproduce and maintain a range of conditions, including reservoir conditions, for core analysis.

SUMMARY

Analysis of core plugs obtained from a reservoir or formation may be useful in evaluating properties of the rock formation, the reservoir hydrocarbons, and other aspects. In some instances, it may be desirable to evaluate the performance of secondary oil recovery processes, such as water flooding, tertiary oil recovery processes, such as gas infection and chemical flooding, and conformance control by plugging agents in high permeable zones. Additionally, it may be desirable to evaluate the performance of such processes at specific temperature and pressures.

In some embodiments, a dual core flooding apparatus for analyzing a plurality of core plugs is provided. The apparatus includes a first core holder and a second core holder. Each core holder is operable to contain at least one core plug of the plurality of core plugs. Each core holder includes an inlet port operable to receive at least one fluid into the core holder and into contact with the core plug and an outlet port operable for removal of the at least one fluid from the core holder. The apparatus further includes a fluids delivery system in fluid communication with the inlet port. The fluids delivery system is operable to introduce the at least one fluid into at least one of the first core holder and the second core holder through the respective inlet port. The apparatus also includes a first separator operable to separate hydrocarbon fluid from the at least one fluid and in fluid communication with the outlet port of the first core holder. The apparatus also includes a second separator operable to separate hydrocarbon fluid from the at least one fluid and in fluid communication with the outlet port of the second core holder. Additionally, the apparatus includes a pressure confining system operable to maintain a first confining pressure in the first core holder and a second confining pressure in the second core holder. The apparatus further includes a first back pressure regulation system operable to maintain pore pressure within a core plug contained in the first core holder independent of a pore pressure associated with the second core holder. The apparatus also includes a second back pressure regulation system operable to maintain pore pressure within a core plug contained in the second core holder independent of the pore pressure associated with the first core holder.

In some embodiments, the dual core flooding apparatus includes a density meter coupled to the outlet port of the first core holder and the output port of the second core holder. The density meter is configured to measure a density of the at least one aqueous fluid exiting from the outlet port or the second outlet port. In some embodiments, the dual core flooding apparatus includes a viscosity meter coupled to the outlet port of the first core holder and the output port of the second core holder. The viscosity meter is configured to measure a density of the at least one aqueous fluid exiting from the outlet port or the second outlet port. In some embodiments, the dual core flooding apparatus includes an image capture apparatus. The image capture apparatus an observation viewing cell coupled to the fluids delivery system via at least one valve and a camera configured to capture images of the at least one fluid before the at least one fluid is received by the first core holder. The image capture apparatus may include a pump operable to maintain a confining pressure in the viewing cell. In some embodiments, the fluids delivery system includes at least one fluid accumulator and at least one pump coupled to the at least one fluid accumulator via at least one valve. In some embodiments, the fluids delivery system includes a plurality of valves arranged to define a first fluid flow path from a first fluid accumulator to the inlet port of the first core holder and a second fluid flow path from a second fluid accumulator to the inlet port of the second core holder when a first group of the plurality of valves are open and a second group of the plurality of valves are closed. In some embodiments, the plurality of valves are further arranged to define a third fluid flow path from the first fluid accumulator to the inlet port of the first core holder and a fourth fluid flow path from the first fluid accumulator to the inlet port of the second core holder when a third group of the plurality of valves are open and a fourth group of the plurality of valves are closed. In some embodiments, the dual core flooding apparatus includes a first differential pressure measurement apparatus configured to measure differential pressure across the first core holder and provide a first differential pressure measurement to the data acquisition system and a second differential pressure measurement apparatus configured to measure differential pressure across the second core holder and provide a second differential pressure measurement to the data acquisition system. In some embodiments, the dual core flooding apparatus includes a first effluent measurement system coupled to the first back pressure regulation system. The first effluent measurement system includes a fraction collector configured to measure an amount of liquid effluent produced from the first back pressure regulation system. In some embodiments, the dual core flooding apparatus includes a second effluent measurement system coupled to the second back pressure regulation system. The second effluent measurement system includes a fraction collector configured to measure an amount of liquid effluent produced from the second back pressure regulation system. In some embodiments, the at least one fluid includes live crude oil, dead crude oil, or seawater. In some embodiments, the properties include at least one of a density, a viscosity, an amount of hydrocarbon fluid, and an amount of water. In some embodiments, the data acquisition system is configured to acquire a first differential pressure across the first core holder and a second differential pressure across the second core holder.

In some embodiments, a method for dual core flooding of a plurality of core plugs is provided. The method includes introducing, by a fluids delivery system, at least one fluid into a first core holder and a second core holder. The first core holder is operable to contain a first core plug sample and the second core holder is operable to contain a second core plug. The method further includes separating, by a separator, hydrocarbon fluid from the at least one fluid. The separator is in fluid communication with an outlet port of the first core holder or an outlet port of the second core holder. The method also includes maintaining, by a pressure confining system, a first confining pressure in the first core holder and a second confining pressure in the second core holder. Additionally, the method includes maintaining, by a back pressure regulation system a first pore pressure within the first core plug sample independent of the pore pressure associated with the second core plug. The method further includes acquiring, by a data acquisition system, properties of the at least one fluid exiting from the outlet port of the first core holder or the outlet port of the second core holder.

In some embodiments, the at least one fluid includes a first fluid and a second fluid different than the first fluid, such that introducing, by the fluids delivery system, at least one fluid into a first core holder and a second core holder includes introducing the first fluid into the first core holder and introducing the second fluid into the second core holder. In some embodiments, the fluids delivery system includes a plurality of valves and introducing the first fluid into the first core holder includes opening a first group of the plurality of valves and closing a second group of the plurality of valves to define a first fluid flow path from a first fluid accumulator of the fluids delivery system to the inlet port of the first core holder and a second fluid path from a second fluid accumulator of the fluids delivery system to the inlet port of the second core holder. In some embodiments, the at least one fluid includes a third fluid, such that introducing, by the fluids delivery system, at least one fluid into a first core holder and a second core holder includes introducing the third fluid into the first core holder after introducing the first fluid into the first core holder. In some embodiments, the at least one fluid includes a single fluid, such that introducing, by a fluids delivery system, at least one fluid into a first core holder and a second core holder includes introducing the single fluid into the first core holder and introducing the single fluid into the second core holder. In some embodiments, the fluids delivery system includes a plurality of valves, such that introducing the single fluid into the first core holder and the second core holder includes opening a first group of the plurality of valves and closing a second group of the plurality of valves to define a first fluid flow path from a first fluid accumulator of the fluids delivery system to the inlet port of the first core holder and a second fluid path from the first fluid accumulator of the fluids delivery system to the inlet port of the second core holder. In some embodiments, the method includes introducing, via the fluids delivery system, a foam slug into the first core holder. In some embodiments, the at least one fluid includes live crude oil, dead crude oil, seawater or carbon dioxide. In some embodiments, the properties include at least one of a density, a viscosity, an amount of hydrocarbon fluid, and an amount of water.

In some embodiments, a dual core flooding apparatus for analyzing a plurality of core plugs is provided. The dual core flooding apparatus includes a first core holder containing a first core plug, a second core holder containing a second core plug, and a fluids delivery system configured to inject a first fluid into the first core plug and a second fluid into the second core plug. The dual core flooding apparatus also includes a first back pressure regulation system in fluid communication with the first core holder and configured to maintain a first pore pressure of the first core plug, and a second back pressure regulation system in fluid communication with the second core holder and configured to maintain a second pore pressure of the second core plug, such that the second pore pressure is maintained independently of the first pore pressure. The dual core flooding apparatus also includes a pressure confining system in fluid communication with the first core holder and the second core holder and configured to maintain a first confining pressure in the first core holder and a second confining pressure in the second core holder.

In some embodiments, the dual core flooding apparatus includes a data acquisition system configured to obtain properties of the first fluid after the first fluid exits the first core holder. In some embodiments, the dual core flooding apparatus includes the properties include at least one of a density, a viscosity, an amount of hydrocarbon fluid, and an amount of water. In some embodiments, the data acquisition system is further configured to obtain properties of the second fluid after the second fluid exits the second core holder. In some embodiments, the first fluid includes live crude oil, dead crude oil, seawater or carbon dioxide and the second fluid includes live crude oil, dead crude oil, seawater or carbon dioxide. In some embodiments, the dual core flooding apparatus includes an image capture system positioned between the fluids delivery system and the first core holder. The image capture system includes a camera configured to capture images of the first fluid before injection into the first core holder

BRIEF DESCRIPTION OF THE DRAWINGS

FIGS. 4E-4M are schematic diagrams of orientations of the first core holder and second core holder in accordance with example embodiments of the disclosure;

DETAILED DESCRIPTION

The present disclosure will now be described more fully with reference to the accompanying drawings, which illustrate embodiments of the disclosure. This disclosure may, however, be embodied in many different forms and should not be construed as limited to the illustrated embodiments set forth in the disclosure. Rather, these embodiments are provided so that this disclosure will be thorough and complete, and will fully convey the scope of the disclosure to those skilled in the art.

Embodiments of the disclosure include a dual core flooding apparatus having at least two core holders to enable the simulation of core flooding and physical displacement processes in oil and gas reservoirs at specific reservoir conditions (for example, temperature and pressure). The dual core flooding apparatus may provide for the injection of a single fluid into one core plug, a single fluid into at least two core plugs, multiple fluids into one core plug, and multiple fluids into at least two core plugs. The dual core flooding apparatus may provide for the simultaneous injection of separate fluids into two core plugs. The dual core flooding apparatus may provide for different orientations of the core plugs, such as horizontal orientations, vertical orientations, and angled orientations. The dual core flooding apparatus may provide for the observation of injection fluids and the in-situ measurement during core flooding of density and viscosity at specific reservoir conditions. The dual core flooding apparatus may provide for the separation and measurement of produced oil and water from core plugs. Additionally, the dual core flooding apparatus may provide for the measurement of differential pressures across each tested core plug during core flooding tests. The dual core flooding apparatus may further provide accurate and stable pore pressures in each tested core plug and accurate and stable confining pressures in each core holder.

Dual Core Flooding Apparatus

Figure 1:
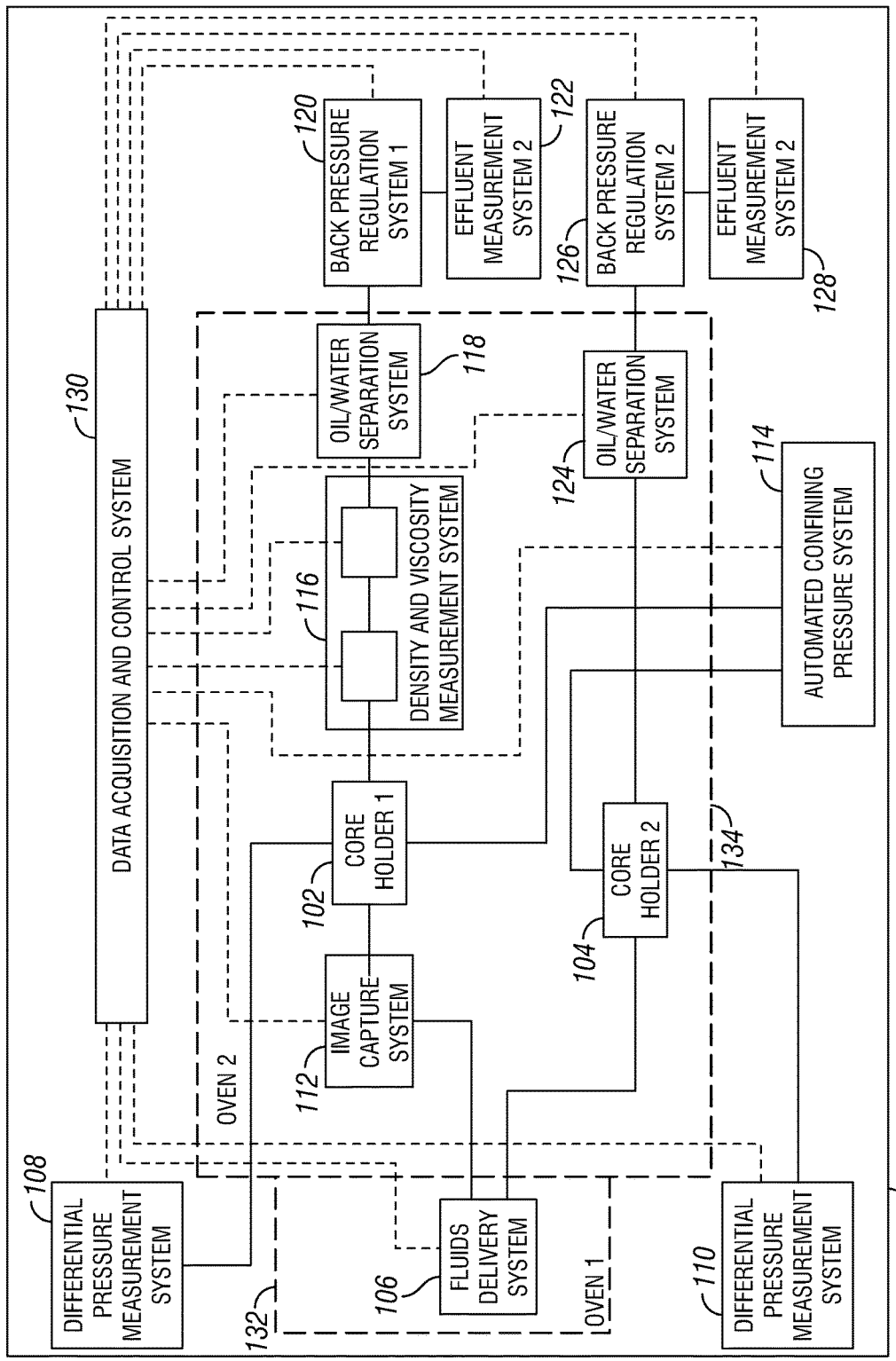
FIG. 1 is a block diagram of a dual core flooding apparatus in accordance with an embodiment of the disclosure.

FIG. 1. depicts a dual core flooding apparatus 100 in accordance with an embodiment of the disclosure, The dual core flooding apparatus 100 may include a first dual core holder 102 and a second dual core holder 104 each arranged to hold a single core plug or composite core plug and receive fluids from a fluids delivery system 106. In some embodiment, the core flooding apparatus 100 may include differential pressure measurement systems 108 and 110 coupled to the first dual core holder 102 and the second dual core holder 104 respectively. In some embodiments, the core flooding apparatus 100 may include an image capture system 112.

As also shown in FIG. 1, in some embodiments, the dual core flooding apparatus 100 may include an automated confining pressure system 114 coupled to the first core holder 102 and the second core holder 104. In some embodiments, the dual core flooding apparatus 100 may include a density and viscosity measurement system 116 coupled to the first core holder 102. In some embodiments, the dual core flooding apparatus 100 may include a first oil/water separation system 118, a first back pressure regulation system 120, a first effluent measurement system 122, a second oil/water separation system 124, a second back pressure regulation system 126, and a second effluent measurement system 128. In some embodiments, the dual core flooding apparatus 100 may include a data acquisition and control system 130 coupled to various components of the apparatus 100

In some embodiments, the dual core flooding apparatus 100 may include one or more ovens to provide heating for fluids, components, and other aspects of the system 100. For example, as shown in FIG. 1, in some embodiments the dual core flooding apparatus 100 may include a first oven 132 arranged to heat the fluids delivery system 106 and a second oven 134 arranged to heat the first core holder 102, the second core holder 104, the image capture system 112, the density and viscosity measurement system 116, the first oil/water separation system 118, and the second oil/water separation system 124. In some embodiments, the first oven 132 and the second oven 134 may be RAD/RFD cabinet ovens manufactured by Despatch Industries of Minneapolis, Minn., USA.

As also shown in FIG. 1, data acquisition and control signal connections are represented by dashed lines. The data acquisition and control system 130 may acquire data from components of the dual core flooding apparatus 100 and may control components of the dual core flooding apparatus 100 (for example, via control signals sent over a network to components of the dual core flooding apparatus 100). As further shown FIG. 1, fluid communication connections are represented by solid lines. As described in the disclosure, various components of the dual core flooding apparatus 100 may be in fluid communication with one another via various arrangements of valves, connectors, and other components.

As described further in the disclosure, the dual core flooding apparatus 100 may enable the simulation of core flooding and physical displacement processes in oil and gas reservoirs at specific reservoir conditions (for example, temperature and pressure). The dual core flooding apparatus 100 may provide the simultaneous injection of separate fluids into two core plugs with varying dimensions and at an injection flow rate in the range of 0.001 cubic centimeters/minute (cc/min) to 15 cc/min. The dual core flooding apparatus 100 may maintain an accurate and stable confining pressure of up to 10000 pounds-per-square inch (psi) and a pore pressure of up to 5000 psi. The dual core flooding apparatus 100 may further provide for an accurate and stable overburden pressure. The dual core flooding apparatus 100 may provide for the observation of injection fluid and the in-situ measurement during core flooding of density and viscosity at specific reservoir conditions. The dual core flooding apparatus 100 may further provide for the separation and measurement of produced oil and water from core plugs. Additionally, the dual core flooding apparatus 100 may provide for the measurement of differential pressures across each tested core plug in the first core holder and the second core holder during core flooding tests. Each of the components of the dual core flooding apparatus is further described in detail.

Fluids Delivery System

FIGS. 2A-2D are schematic diagrams of the fluids delivery system 106 in accordance with an example embodiment of the disclosure. The fluids delivery system 106 may deliver (for example, inject) fluids into core plugs in the core holders 102 and 104 (and into core plugs in each core holder 102 and 104) using one or more pumps and an arrangement of piston accumulators, connectors, and valves. In some embodiments, the fluids delivery system 106 may deliver one or more fluids at a constant flow rate in the range of 0.001 cc/min to 15 cc/min and at a working pressure in the range of 1 psi to 10,000 psi. It should be appreciated that FIGS. 2A-2D depicts merely one embodiment of an arrangement and valves and connectors of the fluids delivery system 106 and other embodiments may include different arrangements of valves and connectors.

As shown in FIGS. 2A-2D, for example, in some embodiments the fluids delivery system 106 may include one or more fluid accumulators 201, 202, 203, 204, and 205, and pumps 206 and 207. In some embodiments, the fluid accumulators 201, 202, 203, 204, and 205 may be piston accumulators manufactured by Coretest Systems, Inc., of Morgan Hill, Calif., USA. In some embodiments, the fluid accumulators 201, 202, 203, 204, and 205 may each have a delivery volume of about 2 liters and a maximum working pressure of about 10,000 psi. In some embodiments, the pumps 206 and 207 may be Quizix Q5000 pumps manufactured by Chandler Engineering of Tulsa, Okla., USA. In some embodiments, the pumps 206 and 207 may have a maximum working pressure of 10,000 psi and a flow rate range of 0.0001 milliliters (ml) ml/minute (min) to 15 ml/min.

The fluids delivery system 106 may include an arrangement of valves and connectors to facilitate selective delivery of one or multiple fluids to the first core holder 102, the second core holder 104, or both. For example, as shown in FIGS. 2A-2D, the first pump 206 may be connected to valves 208 and 209. In some embodiments, valves 208 and 209 may be manual valves. Similarly, the second pump 207 may be connected to valves 210 and 211. In some embodiments, valves 210 and 211 may be manual valves. The valve 209 coupled to the first pump 206 may be a drain valve to enable draining of the lines connected to the first pump 206. The valve 208 may connect the first pump 206 to the fluid accumulators 203, 204, and 205 via the arrangement of valves and cross connectors depicted in FIGS. 2A-2D and described further infra. Similarly, the valve 210 may connect the second pump 207 to the fluid accumulators 203, 204, and 205 and the valve 211 may connect the second pump 207 to the fluid accumulators 201 and 202 via the arrangement of valves and cross connectors depicted in FIGS. 2A-2D and described further infra.

As shown in FIGS. 2A-2D, the first pump 206 may be connected to the fluid accumulators 203, 204, and 205 via valves 212 and 213. The valves 212 and 213 may be connected to the valve 208 and, in some embodiments, may be automatic valves. As also shown in FIG. 2, the second pump 207 may be connected to the fluid accumulators 203, 204, and 205 via the valves 214 and 215. The valves 214 and 215 may be connected to the valve 210 and, in some embodiments, may be automatic valves.

The valves 212, 213, 214, and 215 may be connected to the fluid accumulators 203, 204, and 205 via cross connectors 216 and 217 and the valves 218 and 219, valves 220 and 221, valves 222 and 223, valves 224 and 225, valves 226 and 227, and valves 228 and 229. In some embodiments, the valves 218 and 219, the valves 220 and 221, and the valves 222 and 223 may be automatic valves. In some embodiments, the valves 224 and 225, the valves 226 and 227, and the valves 228 and 229 may be manual valves.

As shown in FIGS. 2A-2D, the second pump 207 may be connected to the fluid accumulators 201 and 202 via the valves 230 and 231. The valves 230 and 231 may be connected to the valve 211 and, in some embodiments, may be automatic valves. The valves 230 and 231 may be connected to the fluid accumulators via the valves 232 and 233 and the valves 234 and 235. In some embodiments, the valves 232 and 233 and the valves 234 and 235 may be manual valves.

The outlets of the fluid accumulators 203, 204, and 205 may be connected to other components of the system 100 via another arrangement of valves and connectors, such as cross connectors 236 and 237. As shown in FIGS. 2A-2D, for example, the fluid accumulator 203 may be connected to cross connectors 236 and 237 by the valves 238 and 239 respectively, the fluid accumulator 204 may be connected to cross connectors 236 and 237 by the valves 240 and 241 respectively, and the fluid accumulator 205 may be connected to cross connectors 236 and 237 by the valves 242 and 243 respectively. In some embodiments, the valves 238 and 239, the valves 240 and 241, and the valves 242 and 243 are manual valves.

As further shown in FIGS. 2A-2D, for example, the fluid accumulator 201 may be connected to the valves 244 and 245, and the fluid accumulator 202 may be connected to the valves 246 and 247. In some embodiments, the valves 244 and 245, and the valves 246 and 247, are manual valves. The valve 245 may be connected to the automatic valve 248, and the valve 246 may be connected to the automatic valve 249. The fluids delivery system 106 also includes the valves 250 and 251. The automatic valves 248 and 249 may be connected to the valve 250. In some embodiments, the valve 251 may be drain valve. In some embodiments, the valves 250 and 251 are manual valves. As also shown in FIGS. 2A-2D, the valves 250 and 251 may be connected to the automatic valve 252, and the cross connector 236 may be connected to the automatic valve 253.

The automatic valves 252 and 253 may be connected to the automatic valves 254 and 255, which in turn are connected to the image capture system 112 and the second dual core holder 104 respectively, as shown by connection blocks A and B and as described further in the disclosure. Similarly, the cross connector 237 may be connected to the automatic valves 256 and 257, which are turn are connected to the first core holder 102 and the second core holder 104 respectively, as shown by connection block C in FIG. 2A.

Figure 2A:
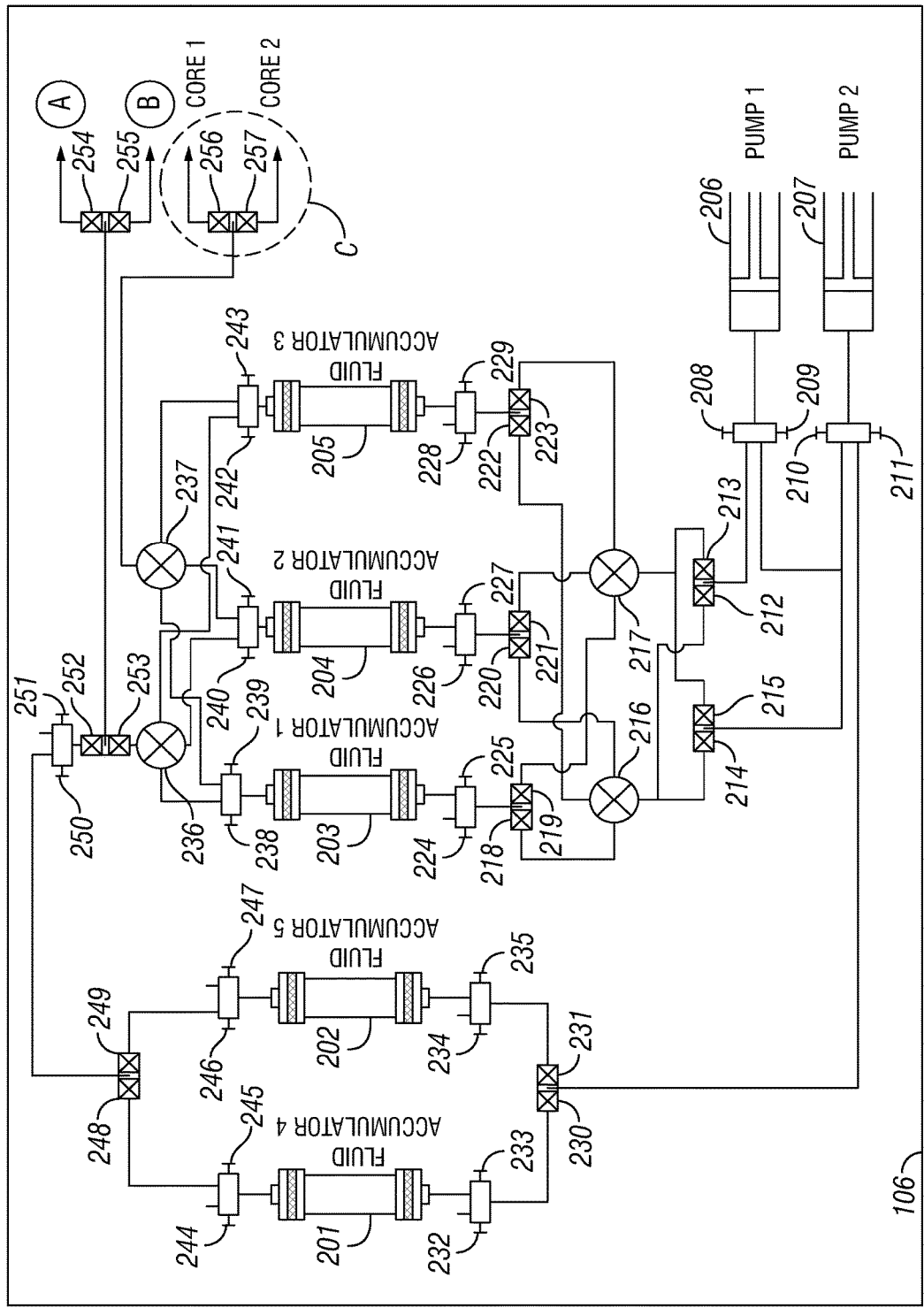
FIGS. 2A-2D are schematic diagrams of a fluids delivery system of the dual core flooding apparatus of FIG. 1 in accordance with an embodiment of the disclosure.
Figure 2B:
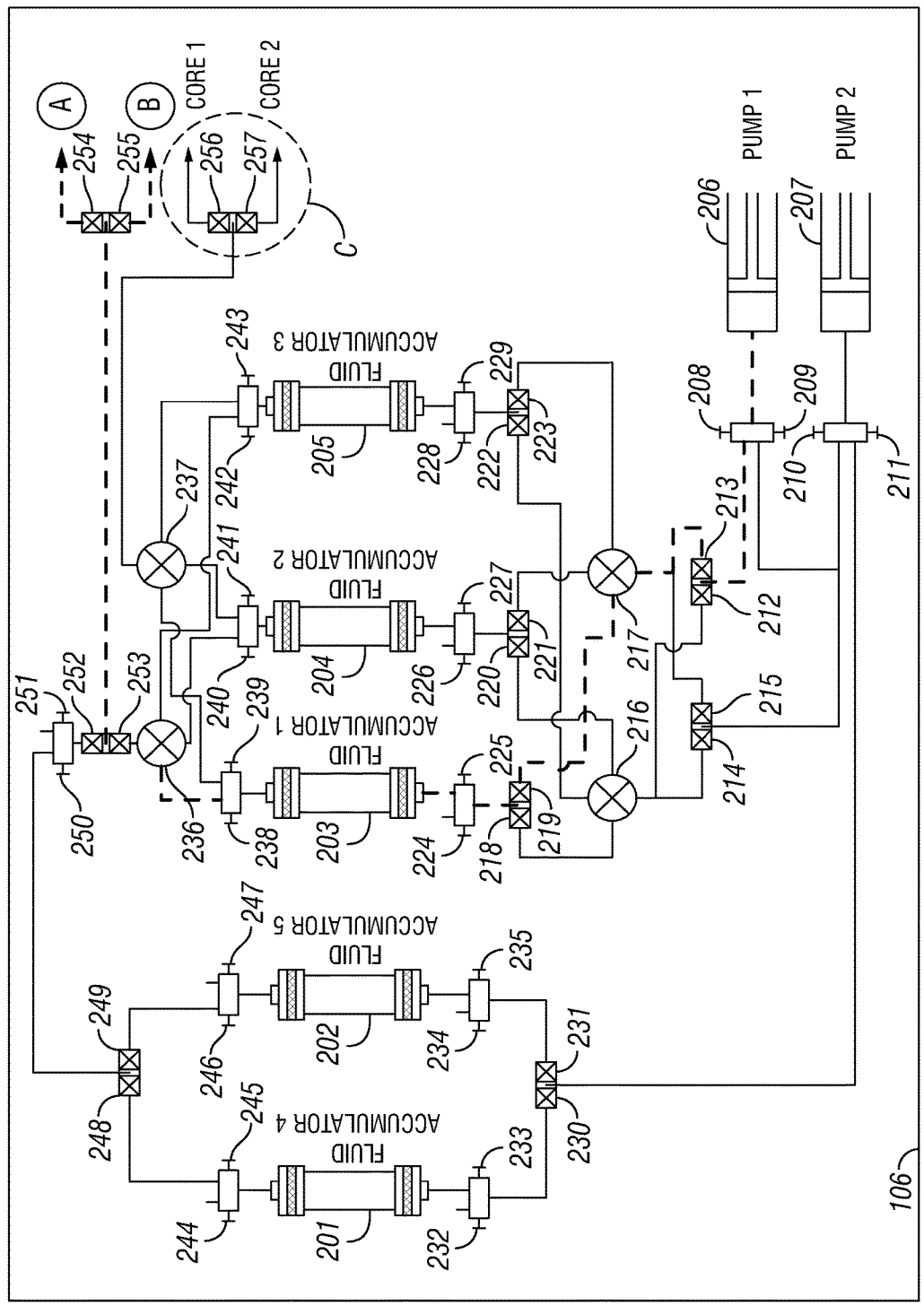

FIG. 2B depicts an example of the delivery of a single fluid into two core plugs (that is, into a core plug in the first core holder 102 and a core plug in the second core holder 104) using the fluids delivery system 106. The fluid path is shown by dashed line 260 depicted in FIG. 2B. As shown in FIG. 2, the pump 206 may be used to pressurize through the valve 208, through the automatic valve 213, through the connector 217, and through the automatic valves 219 and 225 to the fluid accumulator 203. The fluid is pumped from the fluid accumulator 203, through the valve 238, through the connector 236, and through the automatic valve 253 to the automatic valves 254 and 255. Some of the fluid will flow through automatic valve 254 to the image capture system 112 and then to the first core holder 102 (as shown by connection block A in FIGS. 2B and 3), while the other portion of the fluid will flow through the automatic valve 255 to the second core holder 104 (as shown by connection block B in FIGS. 2B and 4B).

Figure 2C:
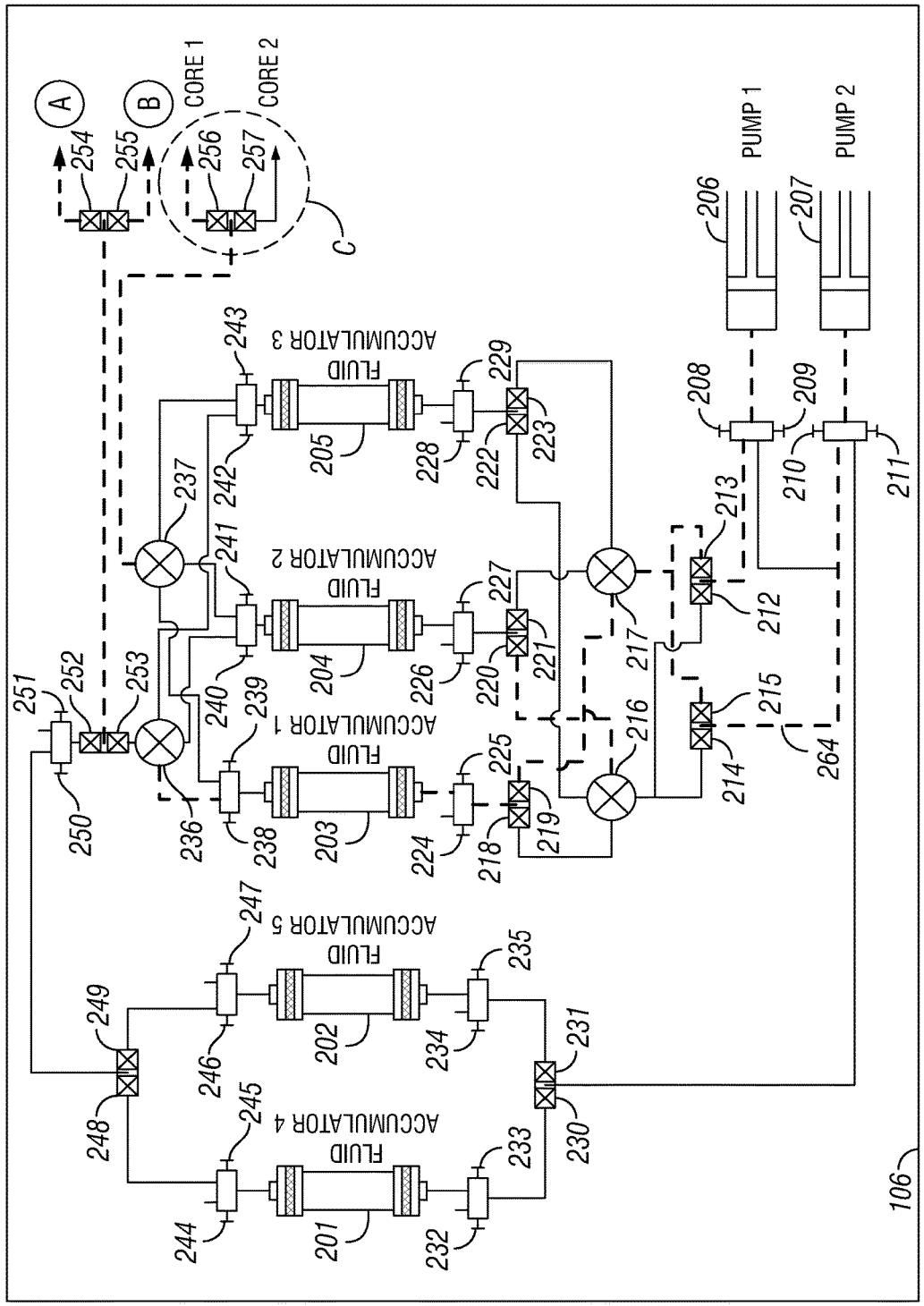

FIG. 2C depicts an example of the simultaneous injection of two fluids into one core plug (that is, into a core plug in the first core holder 102) using the fluids delivery system 106. The fluid paths are shown by dashed lines 262 and 264 depicted in FIG. 2C. The first pump 206 may be used to deliver the first fluid from the fluid accumulator 203, and the second pump 207 may be used to deliver the second fluid from the fluid accumulator 204. The first fluid may be injected using pump 206 to pressurize through the valve 208, through the automatic valve 213, through the connector 217, and through the automatic valves 219 and 225 to the fluid accumulator 203. The fluid is pumped from the fluid accumulator 203, through the valve 238, through the connector 236, and through the automatic valve 253 to the automatic valves 254 and 255. The fluid flows through valve 254 and valves 300 and 302 shown in FIG. 3 to the image capture system 112 and then to the first core holder 102 (as shown by connection block A in FIG. 2C). The valve 255 may be closed to prevent fluid from being delivered to the second core holder 104 (as shown by connection block B in FIGS. 2C and 4C). The second fluid may be injected using pump 207 to pressurize through the valve 210, through the automatic valve 214, through the connector 216, and through the valves 220 and 227 to the fluid accumulator 204. The fluid is pumped from the fluid accumulator 204, through the valve 241, through the connector 237, and through the automatic valve 256 to the first core holder 102 (as shown by connection block C in FIGS. 2C and 4C). The automatic valve 257 may be closed to prevent the second fluid from being delivered to the second core holder 104.

Figure 2D:
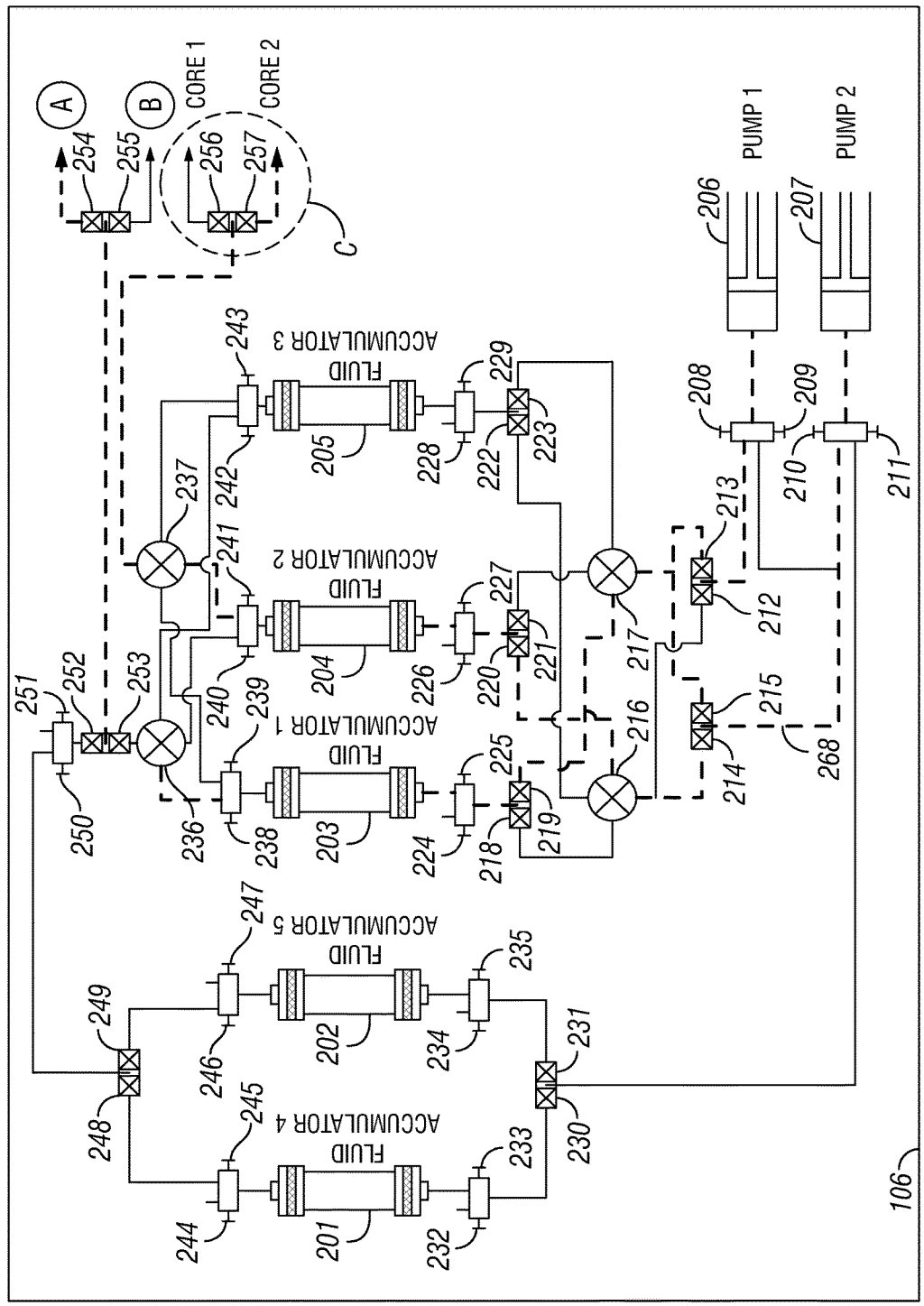
Figure 3:
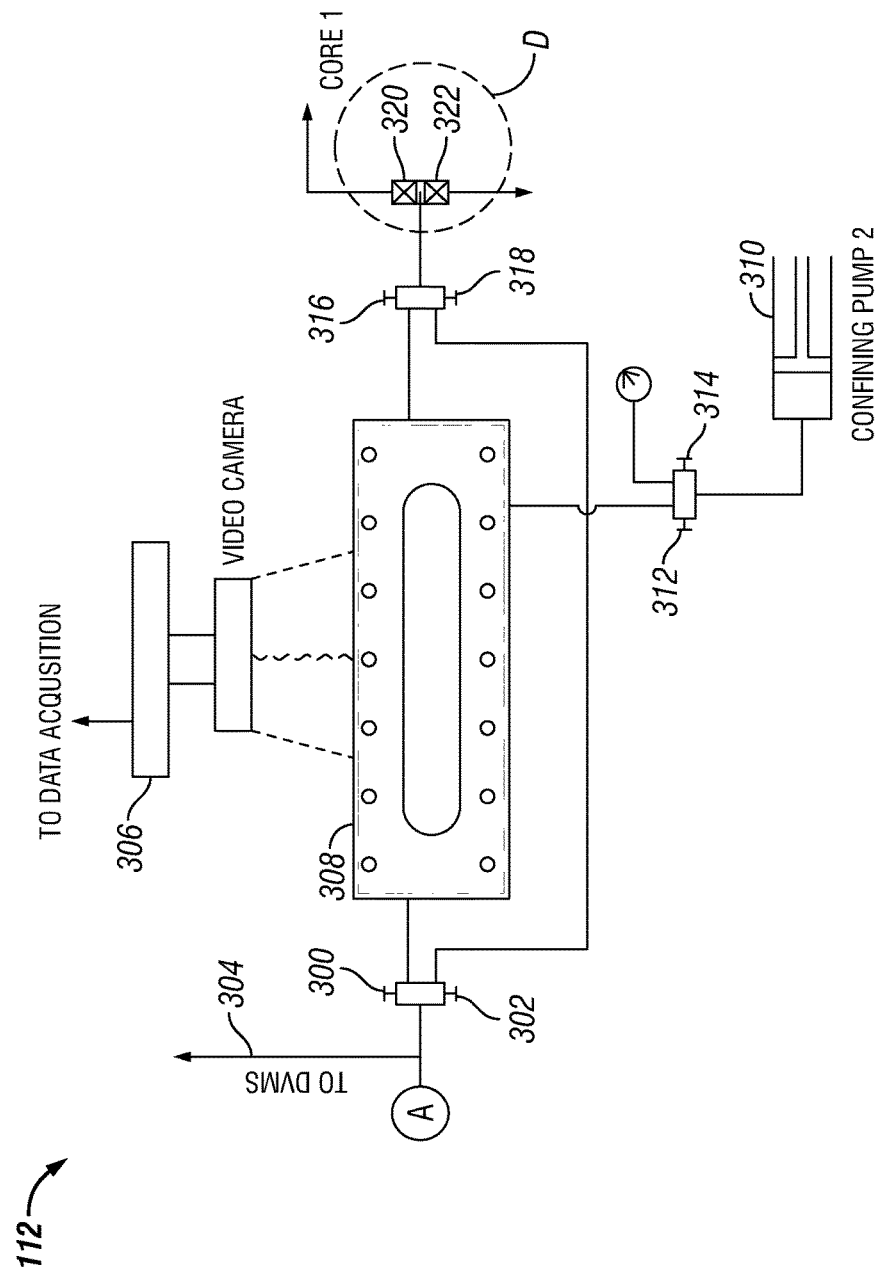
FIG. 3 is a schematic diagram of the image capture system of the dual core flooding apparatus in FIG. 1 in accordance with an example embodiment of the disclosure.

FIG. 2D depicts an example of the simultaneous injection of a first fluid into one core plug (that is, into a core plug in the first core holder 102) and a second fluid into a second core plug (that is, into a core plug in the second core holder 104) using the fluids delivery system 106. The fluid paths are shown by dashed lines 266 and 268 depicted in FIG. 2D. The first pump 206 may be used to deliver the first fluid 266 from the fluid accumulator 203, and the second pump 207 may be used to deliver the second fluid 268 from the fluid accumulator 204. The first fluid 266 may be injected using pump 206 to pressurize through the valve 208, through the valve 213, through the connector 217, and through the automatic valves 219 and 225 to the fluid accumulator 203. The first fluid 266 is pumped from the fluid accumulator 203, through the valve 238, through the connector 236, and through the automatic valve 253 to the automatic valve 254. As shown in FIG. 3 by connection block A and discussed infra, the fluid flows through automatic valve 254 to the image capture system 112 and then to the first core holder 102. The second fluid 268 may be injected using pump 207 to pressurize through the valve 210, through the automatic valve 214, through the connector 216, and through the automatic valves 220 and 227 to the fluid accumulator 204. The second fluid 268 is pumped from the fluid accumulator 204, through the valve 241, through the connector 237, and through the automatic valve 257 to the second core holder 104 (connection block C in FIGS. 2D and 4D). The valve 256 may be closed to prevent the second fluid from being delivered to the first core holder 102.

Image Capture System

FIG. 3 depicts a schematic diagram of the image capture system 112 in accordance with an example embodiment of the disclosure. The image capture system 112 may enable the monitoring and observation of fluids or other substances (for example, chemical solutions such as foaming gels) before injection of the fluids or other substances into core plugs in the core holders 102 and 104. The image capture system 112 may be in fluid communication with the fluids delivery system 106 and the core holder 102 and may include an arrangement of valves that route fluid through an observation cell or bypass the viewing cell. The image capture system 112 may be connected to the automatic valve 254, as shown by connection block A in FIGS. 2A-2D and FIG. 3. The automatic valve 254 may be coupled to the valves 300 and 302 shown in FIG. 3. In some embodiments, the valves 300 and 302 are manual valves. In some embodiments, as shown by line 304, at least a portion of the fluid routed to the image capture system 112 may be routed to the density and viscosity measurement system 116.

The image capture system 112 may include a camera 306, a viewing cell 308, and a pump 310. In some embodiments, the camera 306 may be a camera having a charged-coupled device (CCD) image sensor. The pump 310 may be connected to the valves 312 and 314. In some embodiments, the valves 312 and 314 are manual valves. The viewing cell 308 may be connected to the valve 316. In some embodiments, the viewing cell 308 may have a maximum operating temperature of about 150° C. and a maximum working pressure of about 6000 psi. The valve 302 may be connected to the valve 318. The valves 302 and 318 may enable the bypass of the viewing cell 308. In some embodiments, the valves 316 and 318 are manual valves. The valves 316 and 318 may be connected to the automatic valves 320 and 322. In some embodiments, the valves 320 and 322 are automatic valves. As shown by connection block D in FIG. 3 and FIGS. 4A-4D, the automatic valve 320 may connect the image capture system to the first core holder 102, and the automatic valve 322 may connect the image capture system to the second core holder 104. As shown by connection block D in FIG. 3 and FIGS. 4A-4D, the automatic valve 322 may couple the image capture system 112 to the second core holder 104.

During testing of a core holder, injection fluid may be routed through the automatic valve 254 (shown in FIGS. 2A-2D by connection block A) through the valve 300, and into the viewing cell 308. The video camera 306 may capture video, still images, or both of the fluid in the viewing cell 308 and provide the capture video, still images, or both to the data acquisition and control system 130. The fluid may exit the viewing cell and be routed through the valve 316, through the automatic valve 320, and to the first core holder 102, as shown by connection block D in FIG. 3 and FIGS. 4A-4D. The confining pressure in the viewing cell may be controlled by the pump 310. In some embodiments, the pump 310 may be hand pump. In some embodiments, the pump 310 may be used to equalize the pressure inside the viewing cell 308 with the pressure outside the viewing cell 308 to protect the viewing cell 308. To bypass the viewing cell 308, the fluid may be routed through the valve 302 and through the valve 318, and then to the first core holder 102, the second core holder 104, or both simultaneously, as shown by connection block D. To bypass the viewing cell 308, the valve 300 and the valve 316 may be closed.

Core Holders

FIGS. 4A-4D are schematic diagrams of the first core holder 102, the second core holder 104, and other components in accordance with an example embodiment of the disclosure. In some embodiments, the core holders 102 and 104 may each be configured as a standard Hassler core holder having a fixed axial confining stress. In some embodiments, each core holder 102 and 104 may have a sleeve material compatible with CO2 injection and chemical solution injections and may have a hydrostatic loading condition. In some embodiments, the core holders 102 and 104 may each have a maximum working pressure of 10,000 psi. In some embodiments, the core holders 102 and 104 may each accommodate a core plug of up to 3.8 centimeters (cm) in diameter and in the range of 5 cm to 45 cm in length. In some embodiments, the core holders 102 and 104 may each have three inlets and three outlets. The core holders 102 and 104 may also include various connections for pressure sensing and control, such as via the automated confining pressure system 114. In some embodiments, the core holders 102 and 104 may each be adjusted relative to a vertical axis, a horizontal axis, or both, and relative to each other. For example, in some embodiments the core holder 102 and the core holder 104 may be adjusted to be horizontal and parallel. In some embodiments, the core holder 102 and the core holder 104 may be adjusted to be vertical, parallel, and at angles. In some embodiments, the core holder 102 and the core holder 104 may be vertical and at the same height.

As shown in FIGS. 4A-4D, each core holder 102 and 104 may be connected to an arrangement of valves to control the delivery of fluid to the core holders. For example, FIGS. 4A-4D illustrates the automatic valves 320 and 322 (also depicted in FIG. 3 as shown by connection block D) and automatic valves 256 and 257 (also depicted in FIGS. 2A-2D as shown by connection block C) that receive and route fluids from other components of the dual core flooding apparatus 100.

The automatic valve 320 may be connected to the valves 408 and 410 and the automatic valve 322 may connected to the valves 416 and 418. In some embodiments, the valves 408 and 410 and the valves 416 and 418 may be manual valves. The automatic valve 256 may be connected to the valves 412 and 414, and the automatic valve 257 may be connected to the valves 420 and 422. In some embodiments, the valves 412 and 414 and the valves 420 and 422 may be manual valves. As shown in FIG. 2, the core holders 102 and 104 may be coupled to the automated confining pressure system 114. The automated confining pressure system 114 is connected to the valves 424 and 426. In some embodiments, the valves 424 and 426 are manual valves. In some embodiments, automated confining pressure system 114 may be a PCI-112 manufactured by Coretest Systems, Inc., of Morgan Hill, Calif., USA.

The core holders 102 and 104 may also be connected to an arrangement of valves to provide for connection to the differential pressure measurement systems 108 and 110. For example, as shown in FIG. 1, the first core holder 102 may be connected to valve 428 and valve 430. In some embodiments, the valves 428 and 430 are stainless steel valves. The first core holder 102 may also be connected to upstream pressure transducer (USPT) 432 and downstream pressure transducer (DSPT) 434 via the valves 428 and 430 respectively. Similarly, for example, the second core holder 104 may be connected to valve 436 and valve 438. In some embodiments, the valves 436 and 438 are stainless steel valves. The second core holder 104 may also be connected to an USPT 440 and a DSPT 442 via the valves 436 and 438 respectively. The first core holder 102 may also be coupled to a Heise® gauge (HSG) 448, and the second core holder 104 may also be coupled to an HSG 450.

The output of the core holders 102 and 104 may be routed through an arrangement of valves to other components of the dual core flooding apparatus 100. For example. FIGS. 4A-4D depict valves 452 and 454 and valves 456 and 458. In some embodiments, the valves 452 and 454 and valves 456 and 458 are manual valves that enable the bypass of the first core holder 102 and the second core holder 104. An outlet from the core holder 102 and the valves 452 and 454 may be connected to valve 460, and an outlet from the core holder 104 and the valves 456 and 458 may be connected to valve 462. In some embodiments, an outlet from the core holder 104 may be connected to the second oil/water separation system 124, as shown by connection line 464 and connection block E in FIGS. 4A-4D and FIG. 9.

The outlets from the valves 460 and 462 may be connected to automatic valves 466 and 468. The outlet from the automatic valve 466 may be connected to the density and viscosity measurement system 116, as shown by connection block F in FIGS. 4A-4D and FIG. 7. The outlet from the automatic valve 468 may be connected to a bypass of the density and viscosity measurement system 116, as also shown by connection block F.

Figure 4A:
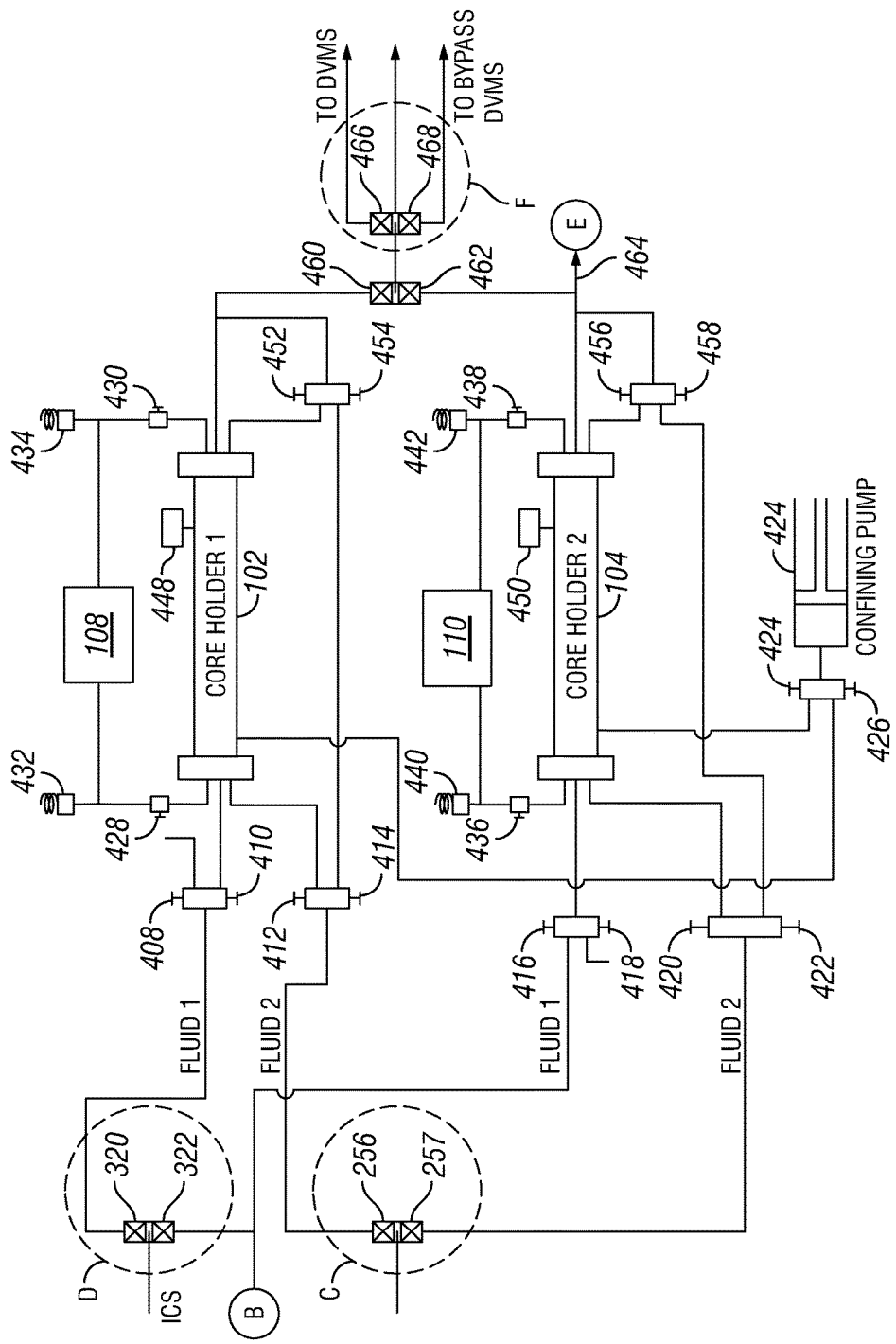
FIGS. 4A-4D are schematic diagrams of a first core holder and second core holder of the dual core flooding apparatus of FIG. 1 in accordance with an embodiment of the disclosure.
Figure 4B:
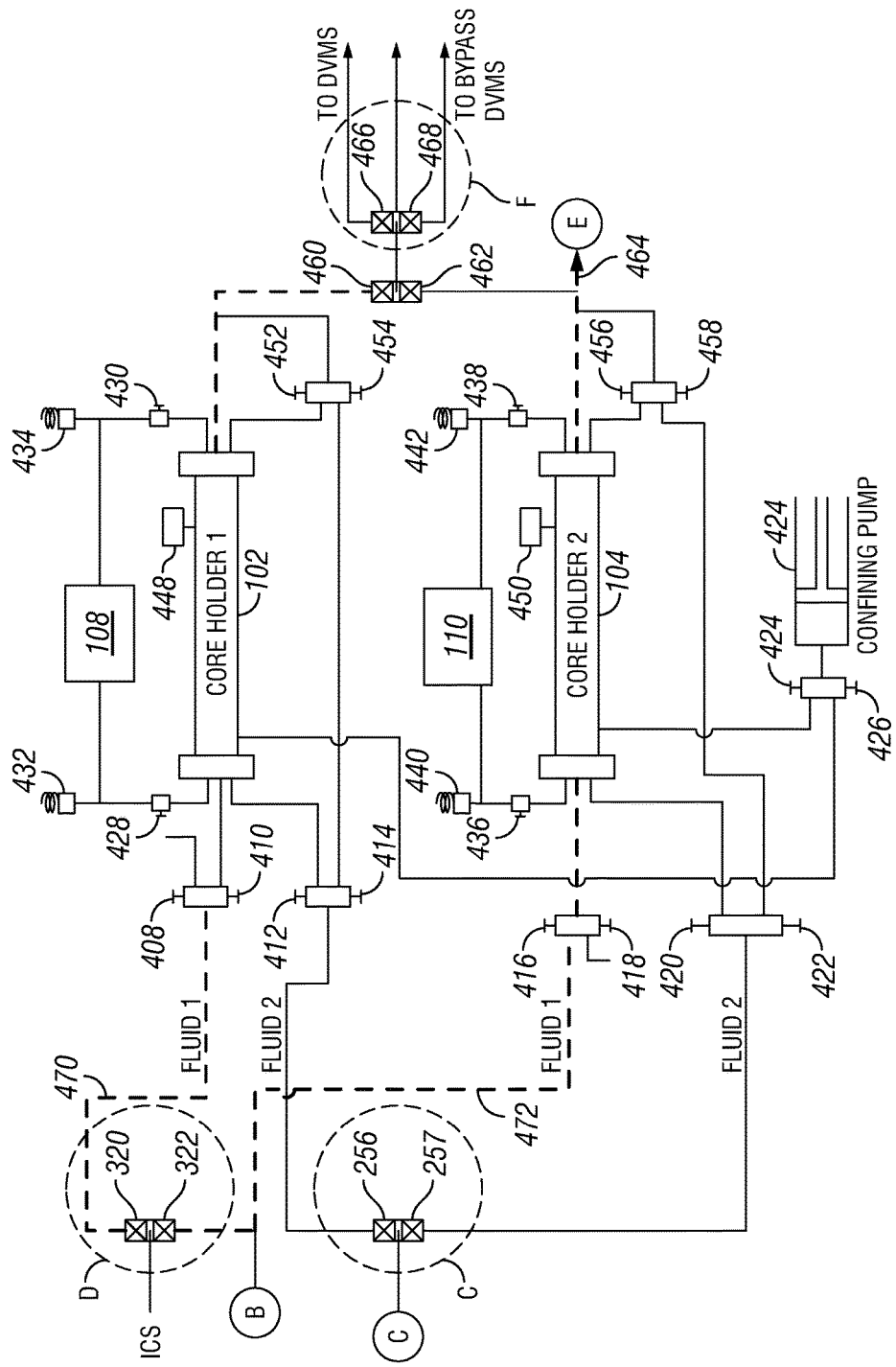

FIG. 4B depicts an example of the injection of a single fluid into core plug in the first core holder 102 and a core plug in the second core holder 104. The example depicted in FIG. 4B corresponds to the example of the fluids delivery system 106 illustrated in FIG. 2B and described supra. As shown by dashed line 470, a portion of the fluid from the image capture system 112 (as shown by connection block D in FIGS. 4A-4D and FIG. 3) may be routed through valve 320 and through the valve 410 to the first core holder 102. The fluid exiting the first core holder 102 may be routed through the valve 460 and either through the automatic valve 466 to the density and viscosity measurement system 116 or through the automatic valve 468 to bypass the density and viscosity measurement system 116 (as shown by connection block F in FIGS. 4A-4D and FIG. 7). As shown by dashed line 472, a portion of the same fluid from the image capture system 112 (as shown by connection block D in FIGS. 4B and 3) may be routed through automatic valve 322 and through the valve 416 to the second core holder 104. As shown by dashed line 464 and connection block E in FIGS. 4B and 9, the fluid exiting the second core holder 104 may be routed to the second oil/water separation system 124.

Figure 4C:
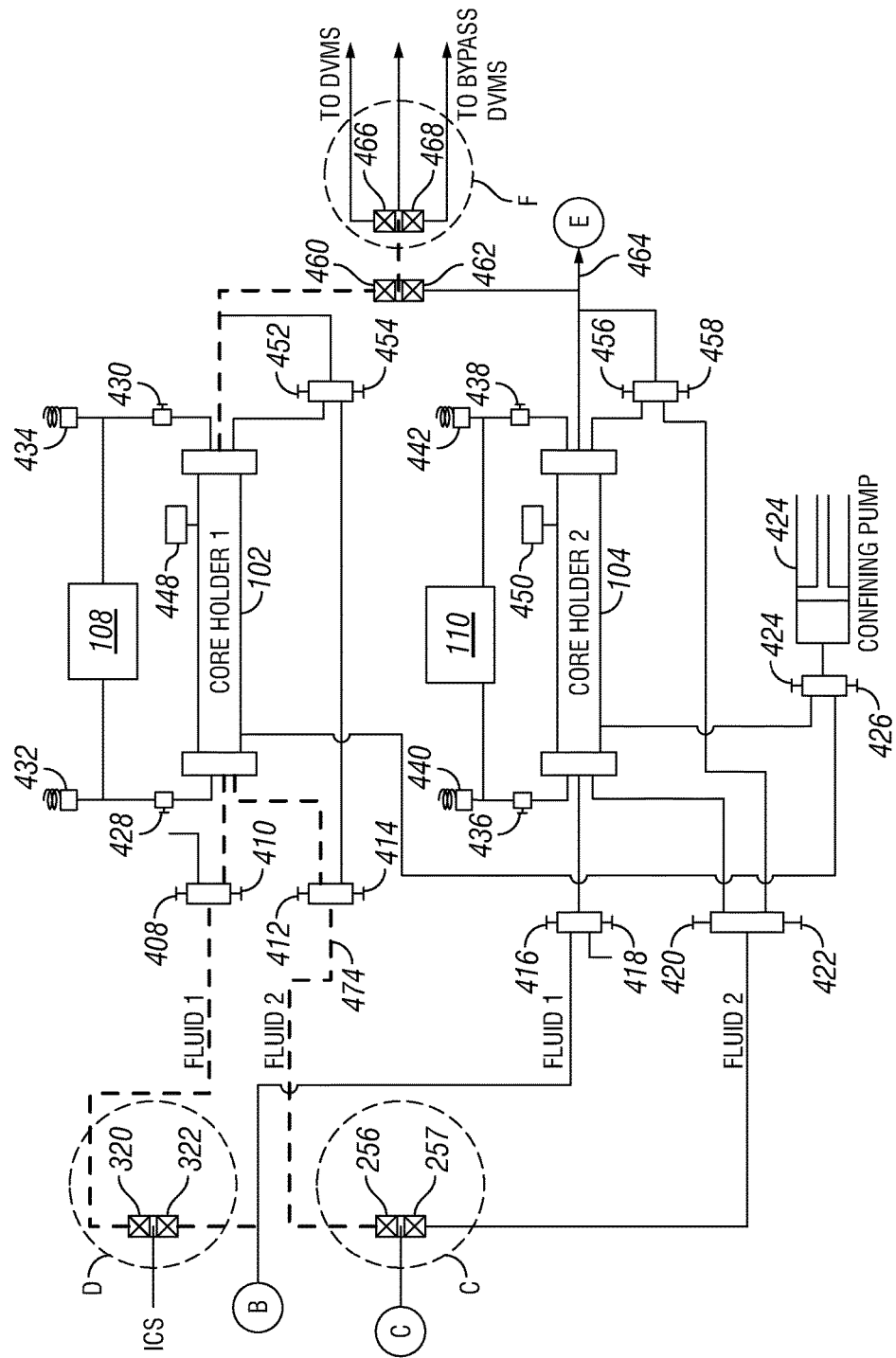

FIG. 4C depicts an example of the injection of the simultaneous injection of two fluids into one core plug (that is, into a core plug in the first core holder 102) using the fluids delivery system 106. The example depicted in FIG. 4C corresponds to the example of the fluids delivery system 106 illustrated in FIG. 2C and described supra. As shown by dashed line 474, a first fluid from the from the fluids delivery system 106 and image capture system 112 (as shown by connection block A in FIG. 2C and FIG. 3, and connection block D in FIG. 3 and FIG. 4C) may be routed through automatic valve 320 and through the valve 410 to the first core holder 102. As shown by dashed line 476, a second fluid from the fluids delivery system 106 (as shown by connection block C in FIG. 2C and FIG. 4C) may be routed through automatic valve 256 and through the valve 412 to the first core holder 102. The fluids exiting the first core holder 102 may be routed through the valve 460 and either through the valve 466 to the density and viscosity measurement system 116 or through the automatic valve 468 to bypass the density and viscosity measurement system 116, as shown by connection block F in FIGS. 4C and 7. In such embodiments, the automatic valve 257 may be closed to prevent the fluids from being routed to the second core holder 104. In another embodiment, both fluids may be routed to the first core holder 102 according to the path shown by dashed line 474.

Figure 4D:
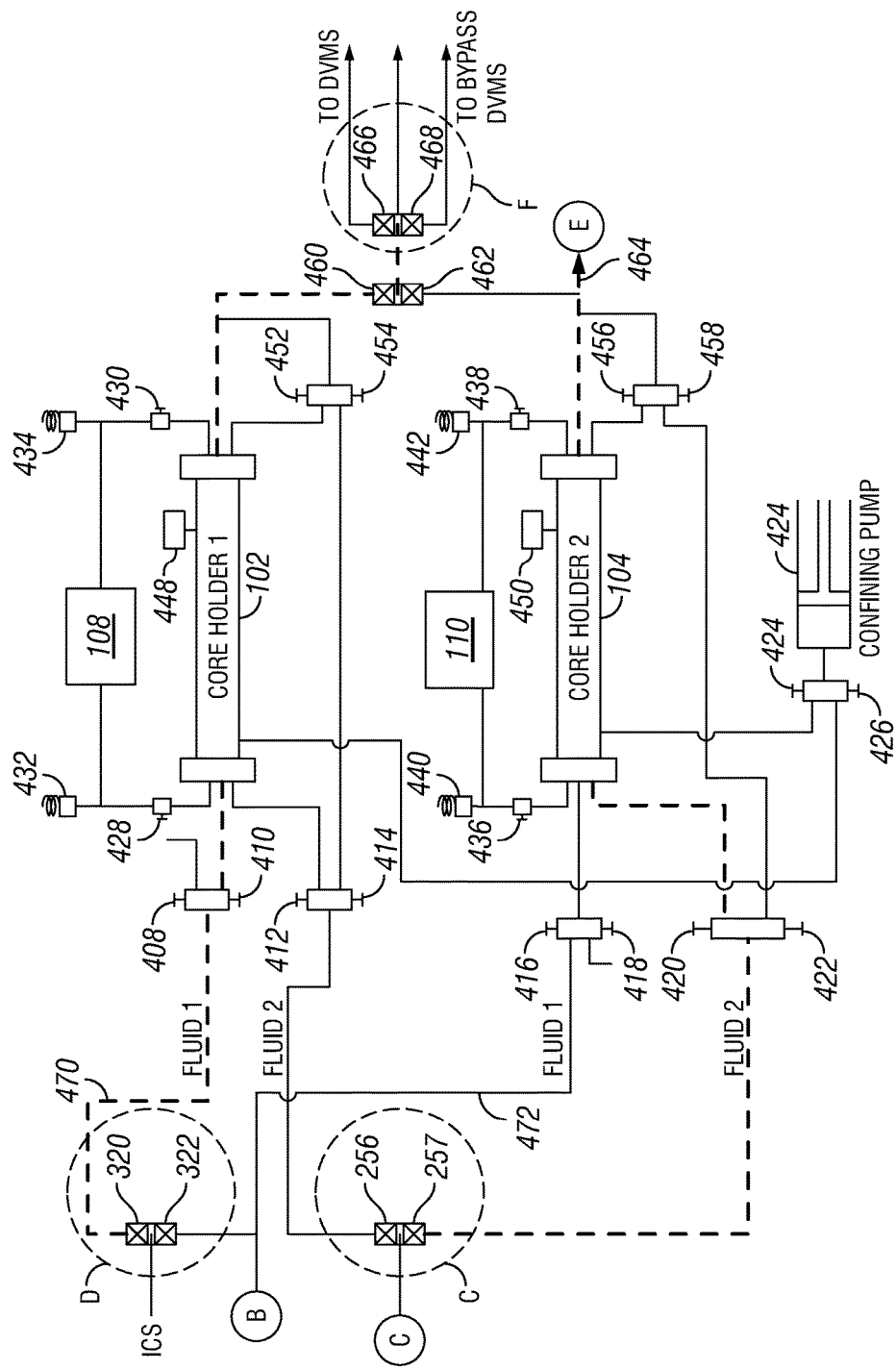

FIG. 4D depicts an example of the simultaneous injection of a first fluid into one core plug (that is, into a core plug in the first core holder 102) and a second fluid into a second core plug (that is, into a core plug in the second core holder 104). The example depicted in FIG. 4D corresponds to the example of the fluids delivery system 106 illustrated in FIG. 2D and described supra. As shown by dashed line 478, a first fluid from the image capture system 112 (as shown by connection block D in FIGS. 3 and 4D) may be routed through automatic valve 320 and through the valve 410 to the first core holder 102. The first fluid may exit the first core holder 102 according to the route described supra. As shown by dashed line 480, the second fluid from the fluids delivery system 106 (as shown by connection block C in FIGS. 2D and 4D) may be routed through the automatic valve 257 and through the valve 420 to the second core holder 104. The second fluid may exit the second core holder 104 according to the route described supra.

As discussed supra, in some embodiments the core holders 102 and 104 may each be adjusted relative to a vertical axis, a horizontal axis, or both, and relative to each other. In some embodiments, the first core holder 102 and the second core holder 104 may each be rotationally mounted on a fixture to enable rotation of the first core holder 102 and the second core holder 104. In such embodiments, for example, the first core holder 102 and the second core holder 104 may be rotated between a horizontal orientation (for example, at a 0° angle relative to a horizontal axis) and a vertical position (for example, at a 90° angle relative to a horizontal axis). In some embodiments, the first core holder 102 may be at a different height than the second core holder 104 (for example, in a horizontal orientation the first core holder 102 may be above the second core holder 104).

FIGS. 4E-4M depict various orientations of the core holders 102 and 104 in accordance with example embodiments of the disclosure. FIGS. 4E-4M also depict delivery of fluids to the core holders 102 and 104 in the various orientations in accordance with the examples described supra and illustrated in FIGS. 4A-4D. It should be appreciated that FIGS. 4E-4M depict the core holders 102 and 104 and fluid flows but omit for clarity the other components of the dual core flooding apparatus 100.

Figure 4E:
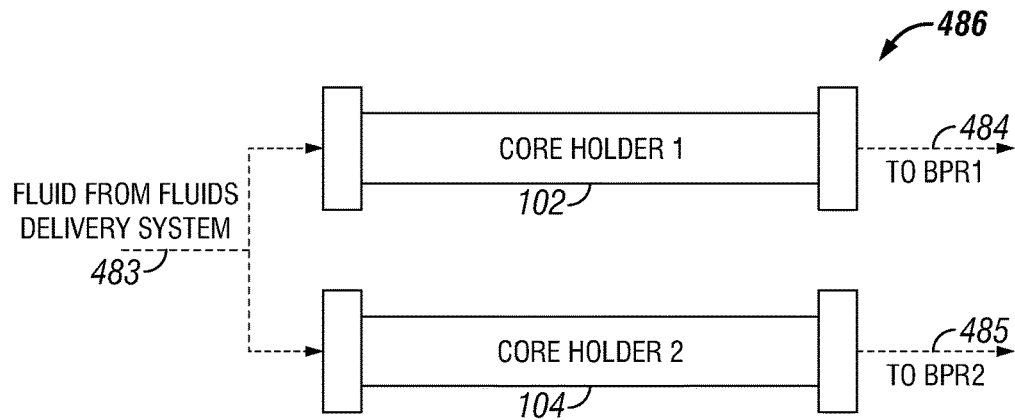
Figure 4F:
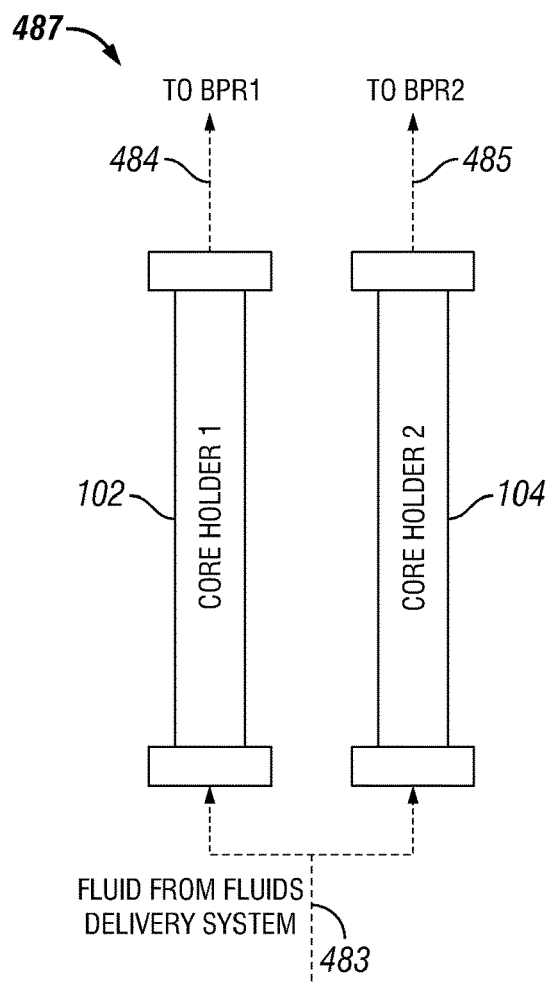
Figure 4G:
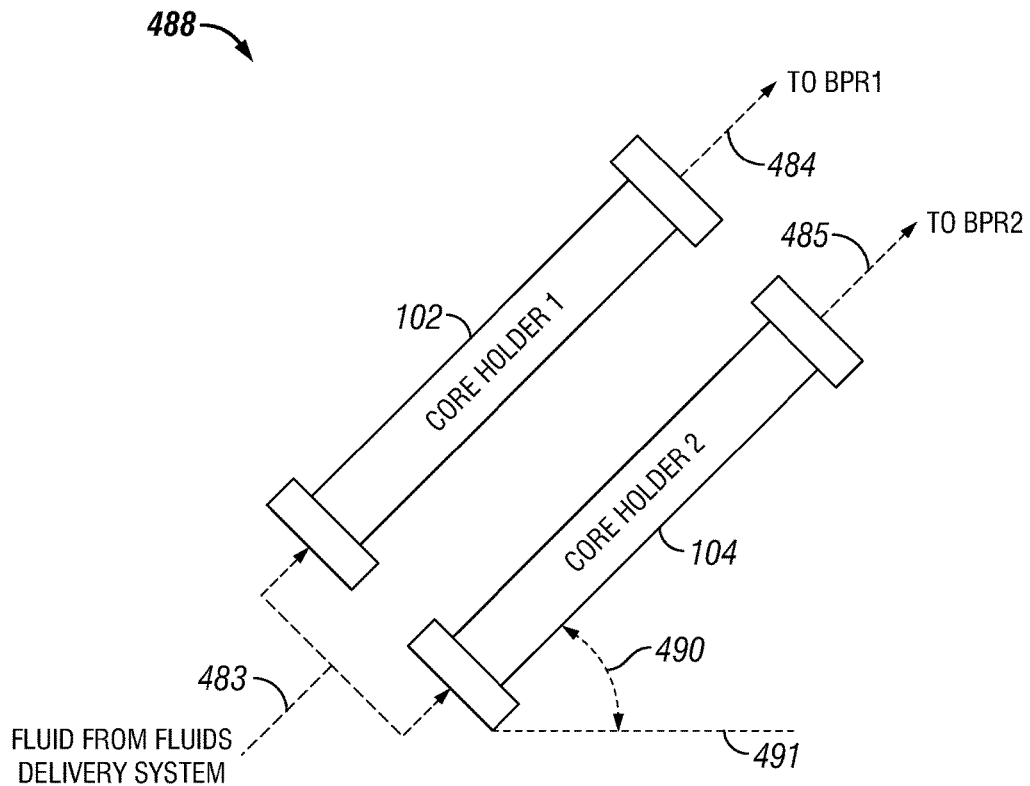

FIGS. 4E-4G depict the core holders 102 and 104 in various orientations and having a single fluid delivered to both core holders 102 and 104 from the fluids delivery system 106, as shown by line 483. As also shown in FIGS. 4E-4G by line 484, the fluid exiting the first core holder 102 may be directed to the first back pressure regulation system 120, as described further in the disclosure. As shown in FIGS. 4E-4G by line 485, the fluid exiting the second core holder 104 may be directed to the second back pressure regulation system 126, as also described further in the disclosure.

FIG. 4E depicts a horizontal orientation 486 of the core holders 102 and 104 in accordance with an example embodiment of the disclosure. In the horizontal orientation 486, the first core holder 102 and the second core holder 104 may be parallel to each other and horizontal relative to the earth, such that the inlet and outlet of the first core holder 102 lie along the same horizontal axis and the inlet and outlet of the second core holder 104 lie along the same horizontal axis.

FIG. 4F depicts a vertical orientation 487 of the core holders 102 and 104 in accordance with an example embodiment of the disclosure. In the vertical orientation 487, the first core holder 102 and the second core holder 104 may be parallel to each other and vertical relative to the earth, such that the inlet and outlet of the first core holder 102 lie along the same vertical axis and the inlet and outlet of the second core holder 104 lie along the same vertical axis.

FIG. 4G depicts an angled orientation 488 of the core holders 102 and 104 in accordance with an example embodiment of the disclosure. In the angled orientation 488, the first core holder 102 and the second core holder 104 may be parallel to each other and angled relative to the earth such that the centerline of each core holder 102 and 104 forms an angle 490 of less than 90° with a horizontal axis (indicated by line 491). In some embodiments, the angle 490 may be 30° or 60°. In some embodiments, the core holders 102 and 104 may be continuously rotated to any angle between 0° and 90°.

Figure 4H:
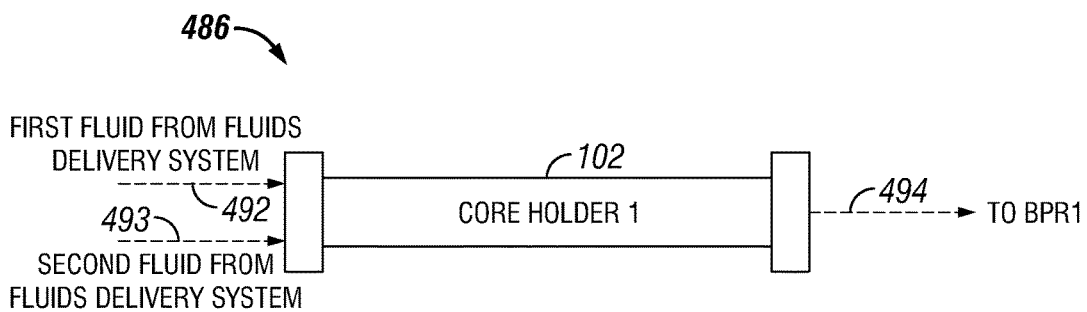

FIGS. 4H-4J depict the core holder 102 in various orientations and having two fluids delivered to the core holder 102 from the fluids delivery system 106. For example, delivery of a first fluid is shown by line 492 and delivery of a second fluid is shown by line 493. As also shown in FIGS. 4H-4J by line 494, the fluids exiting the first core holder 102 may be directed to the first back pressure regulation system 120, as described further in the disclosure. It should be appreciated that the various orientations and delivery of two fluids to the first core holder 102 shown in FIGS. 4H-4J may also be implemented using the second core holder 104 instead of the first core holder 102.

FIG. 4H depicts the horizontal orientation 486 of the first core holders 102 in accordance with an example embodiment of the disclosure. As previously stated, in the horizontal orientation 486, the first core holder 102 may be horizontal relative to the earth, such that the inlet and outlet of the first core holder 102 lie along the same horizontal axis.

FIG. 4I depicts the vertical orientation 487 of the first core holders 102 in accordance with an example embodiment of the disclosure. As previously stated, in the vertical orientation 487, the first core holder 102 may be vertical relative to the earth, such that the inlet and outlet of the first core holder 102 lie along the same vertical axis.

FIG. 4J depicts the angled orientation 488 of the first core holder 102 in accordance with an example embodiment of the disclosure. As previously stated and as shown in FIG. 4J, the first core holder 102 may be angled relative to the earth such that the centerline of the first core holder 102 forms the angle 490 of less than 90° with a horizontal axis (indicated by line 491). In some embodiments, the angle 490 may be 30° or 60°. In some embodiments, the first core holder 102 may be continuously rotated to any angle between 0° and 90°.

Figure 4K:
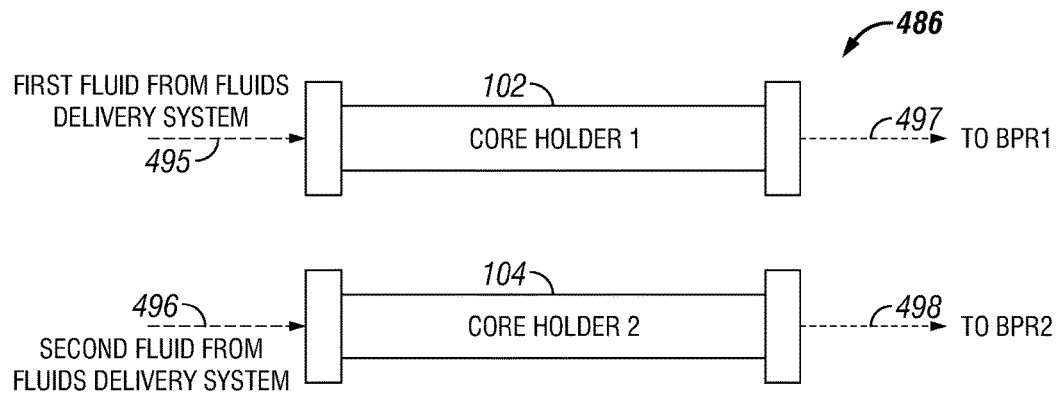
Figure 4L:
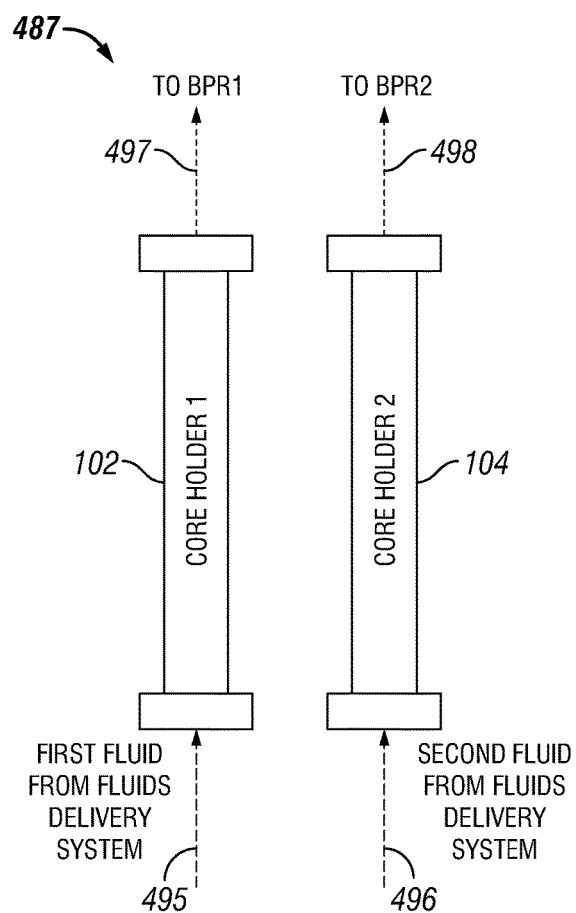
Figure 4M:
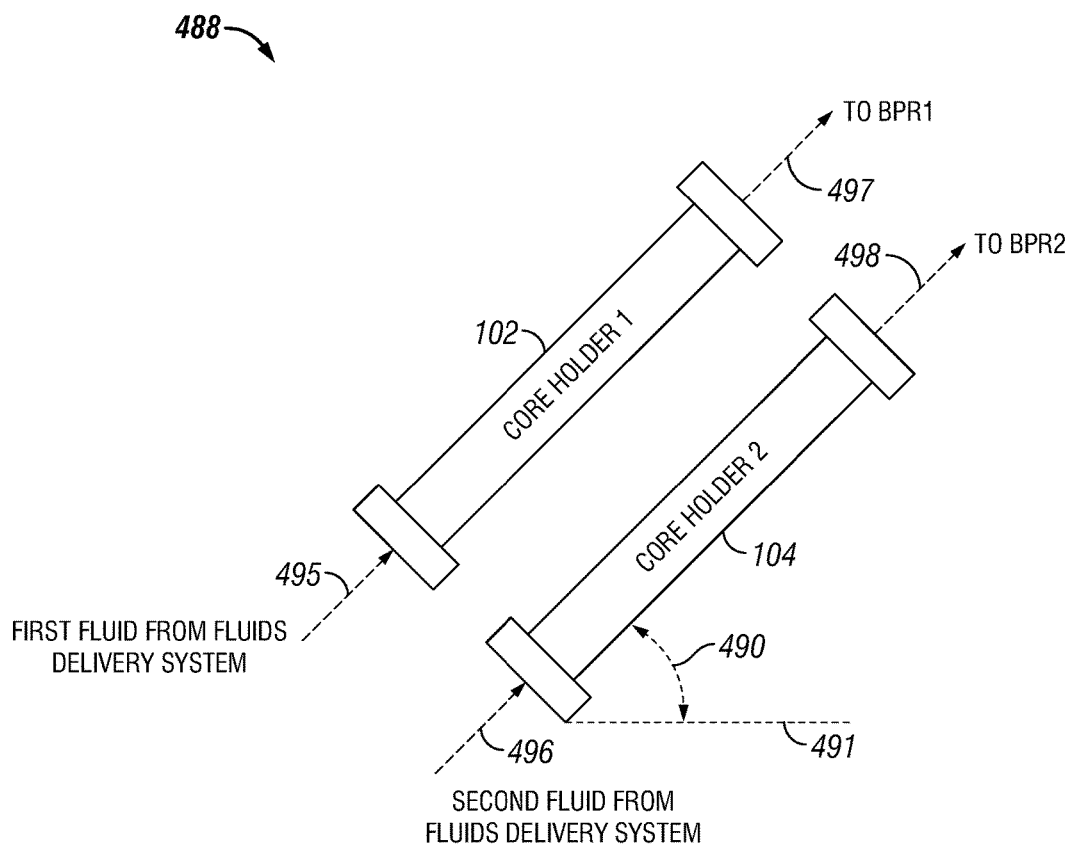

FIGS. 4K-4M depict the core holders 102 and 104 in various orientations and having a first fluid delivered to the first core holder 102 from the fluids delivery system 106, as shown by line 495, and a second fluid delivered to the second core holder 104 from the fluids delivery system 106, as shown by line 496. As also shown in FIGS. 4K-4M by line 497, the first fluid exiting the first core holder 102 may be directed to the first back pressure regulation system 120, as described further in the disclosure. As shown in FIGS. 4K-4M by line 498, the second fluid exiting the second core holder 104 may be directed to the second back pressure regulation system 126, as also described further in the disclosure.

FIG. 4K depicts the horizontal 4K-4M 486 of the core holders 102 and 104 for the delivery of a first fluid to the first core holder 102 and a second fluid to the second core holder 104 in accordance with an example embodiment of the disclosure. As described supra, In the horizontal 4K-4M 486, the first core holder 102 and the second core holder 104 may be parallel to each other and horizontal relative to the earth, such that the inlet and outlet of the first core holder 102 lie along the same horizontal axis and the inlet and outlet of the second core holder 104 lie along the same horizontal axis.

FIG. 4L depicts the vertical 4K-4M 487 of the core holders 102 and 104 for the delivery of a first fluid to the first core holder 102 and a second fluid to the second core holder 104 in accordance with an example embodiment of the disclosure. As described supra, In the vertical 4K-4M 487, the first core holder 102 and the second core holder 104 may be parallel to each other and vertical relative to the earth, such that the inlet and outlet of the first core holder 102 lie along the same vertical axis and the inlet and outlet of the second core holder 104 lie along the same vertical axis.

FIG. 4M depicts an angled orientation 488 of the core holders 102 and 104 for the delivery of a first fluid to the first core holder 102 and a second fluid to the second core holder 104 in accordance with an example embodiment of the disclosure. In the angled orientation 488, the first core holder 102 and the second core holder 104 may be parallel to each other and angled relative to the earth such that the centerline of each core holder 102 and 104 forms the angle 490 that is less than 90° with a horizontal axis (indicated by line 491). As previously mentioned, in some embodiments, the angle 490 may be 30° or 60° and, in some embodiments, the core holders 102 and 104 may be continuously rotated to any angle between 0° and 90°.

Differential Pressure Measurement Systems

Figure 5:
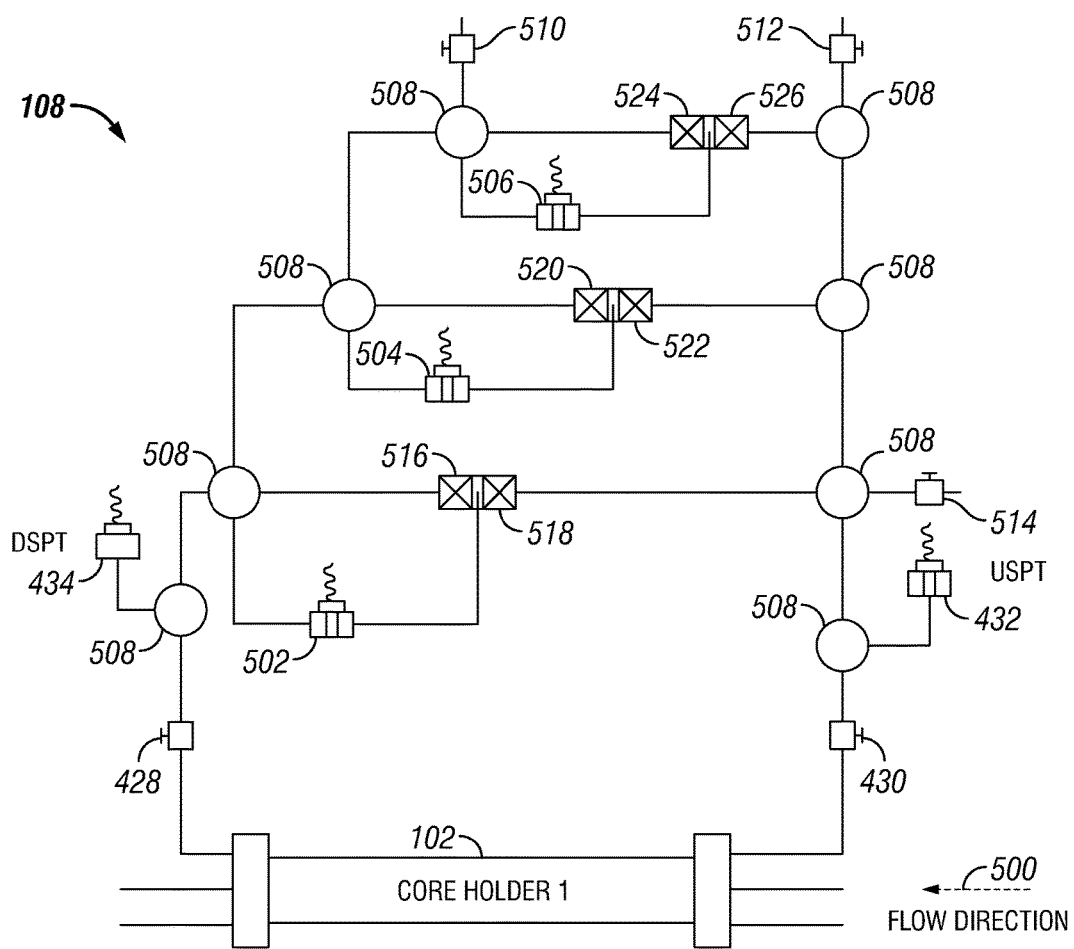
FIG. 5 is a schematic diagram of a first differential pressure measurement system of the dual core flooding apparatus of FIG. 1 in accordance with an embodiment of the disclosure.

FIG. 5 depicts a schematic diagram of the first differential pressure measurement system 108 in accordance with an example embodiment of the disclosure. The first differential pressure measurement system 108 may include three levels of pressure transducers arranged to measure the differential pressure across the core plug in the first core holder, and the inlet pressure and outlet pressure of the first core holder 102.

As shown in FIG. 5, the first core holder 102 may be connected to the first differential pressure measurement system 108 by the valves 428 and 430. The fluid flow direction through the first core holder 102 is depicted by directional arrow 500.

As shown in FIG. 5, the first differential pressure measurement system 108 includes three levels of differential pressure transducers 502, 504, and 506 and the inlet (upstream) and outlet (downstream) pressure transducers 432 and 434 to measure differential pressure across the core plug in the first core holder 102 while running core flooding experiments. In some embodiments, the inlet pressure transducer 432 and the outlet pressure transducer 434 may be pressure transducers manufactured by Quartzdyne of Salt Lake City, Utah, USA. In some embodiments, the inlet pressure transducer 432 and the outlet pressure transducer 434 may be pressure transducers manufactured by Setra Systems, Inc. of Boxborough, Mass., USA. In some embodiments, the pressure transducers may have an accuracy of about 0.01%. In some embodiments, the pressure transducers 432 and 434 have a maximum working pressure of about 10,000 psi.

In some embodiments, the differential pressure transducers 502, 504, and 506 may be stainless steel transducers. In some embodiments, the differential pressure transducers 502, 504, and 506 may have an accuracy of about 0.5% or, in some embodiments, about 0.1%. In some embodiments, the first pressure transducer 502 may have a range of 0 psid to 5 psid, the second pressure transducer 504 may have a range of 0 psid to 50 psid, and the third pressure transducer 506 may have a range of 0 psid to 500 psid. In some embodiments, the differential pressure transducers 502, 504, and 506 may be Barton Instruments pressure transducers manufactured by Cameron International Corporation of Houston, Tex., USA. In some embodiments, the differential pressure transducers 502, 504, and 506 may be Barton Instruments pressure transducers manufactured by Cameron International Corporation of Houston, Tex., USA. In some embodiments, the differential pressure transducers 502, 504, and 506 manufactured by Validyne Engineering of Northridge, Calif., USA.

FIG. 5 also depicts an arrangement of cross connectors 508 that connect the valves and transducers in the manner depicted in the figure. The first differential pressure measurement system 108 includes valves 510, 512, and 514 that operate as filling and flushing valves for the first differential pressure measurement system 108. Each differential pressure transducer may be connected to bypass valves to protect the differential pressure transducers from overpressure conditions. For example, the differential pressure transducer 502 may be connected to valves 516 and 518. Similarly, the differential pressure transducer 504 may be connected to valves 520 and 522, and the differential pressure transducer 506 may be connected to valves 524 and 526. For example, if the first differential pressure transducer 502 detects an overpressure condition, the valve 516 connected to the upstream pressure source may be automatically opened to connect the negative side of the transducer 502 to the upstream pressure source. The valve 518 may be automatically closed to isolate the transducer 502 to the downstream pressure source, such that both sides of the transducer 502 are opened to the upstream pressure source and the differential pressure will be zero to protect the transducer 502. The valve 522 may be automatically opened such that the second differential pressure transducer 504 having the greater pressure range may be engaged to measure the differential pressure. The valves 520, 522, 524, and 526 may thus operate in a similar manner to protect the valves 504 and 506 from overpressure conditions and engage the third differential pressure transducer 506 to measure the differential pressure.

Figure 6:
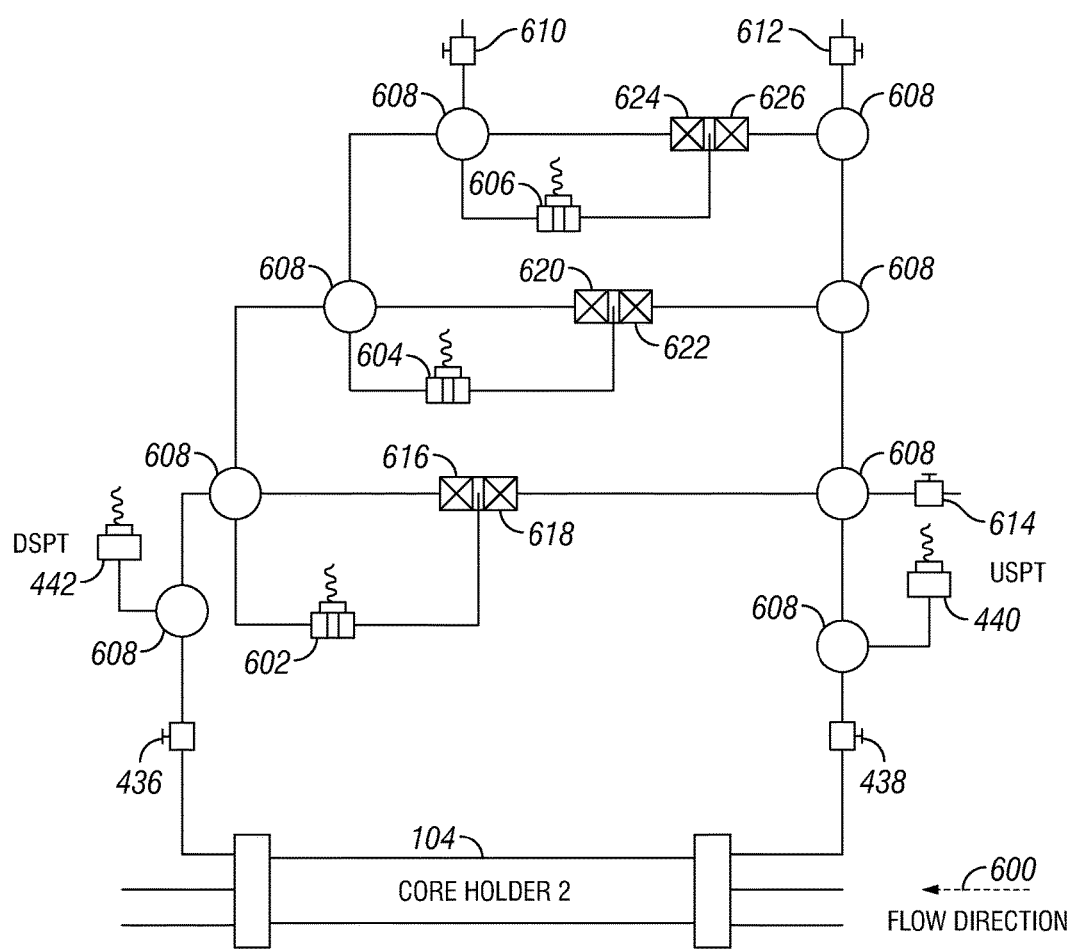
FIG. 6 is a schematic diagram of a second differential pressure measurement system of the dual core flooding apparatus of FIG. 1 in accordance with an embodiment of the disclosure.

FIG. 6 depicts a schematic diagram of the second differential pressure measurement system 110 in accordance with an example embodiment of the disclosure. As will be appreciated, the second differential pressure measurement system 110 may include similar components to that of the first differential pressure measurement system 108 and may operate in a similar manner. The second differential pressure measurement system 110 may include pressure transducers arranged to measure the pore pressure (that is, the inlet pressure of the core plug in the second core holder 104), the inlet pressure and outlet pressure of the second core holder 104, and the differential pressure across the core plug in the second core holder 104 during testing.

As shown in FIG. 6, the second core holder 104 may be connected to the second differential pressure measurement system 110 by the valves 436 and 438. The fluid flow direction through the second core holder 104 is depicted by directional arrow 600.

As depicted in FIG. 6, the second differential pressure measurement system 110 includes three levels of differential pressure transducers 602, 604, and 606 to measure differential pressure across the core plug in the second core holder 104, and the inlet and outlet pressure transducers 440 and 442 to measure upstream and downstream pressures for the second core holder 104 while running core flooding experiments. In some embodiments, the inlet pressure transducer 440 and the outlet pressure transducer 442 may be pressure transducers manufactured by Quartzdyne of Salt Lake City, Utah, USA. In some embodiments, the pressure transducers may have an accuracy of about 0.01%. In some embodiments, the differential pressure transducers 602, 604, and 606 may be stainless steel transducers. In some embodiments, the differential pressure transducers 602, 604, and 606 may have an accuracy of about 0.5%. In some embodiments, the first pressure transducer 602 may have a range of 0 psid to 5 psid, the second pressure transducer 604 may have a range of 0 psid to 50 psid, and the third pressure transducer 606 may have a range of 0 psid to 500 psid.

FIG. 6 also depicts an arrangement of cross connectors 608 that connect the valves and transducers in the manner depicted in the figure. As also shown in FIG. 6, the second differential pressure measurement system 110 includes valves 610, 612, and 614 that operate as filling and flushing valves for the second differential pressure measurement system 110. Each differential pressure transducer may be connected to bypass valves to protect the differential pressure transducers from overpressure conditions. For example, the differential pressure transducer 602 may be connected to automatic valves 616 and 618. Similarly, the differential pressure transducer 604 may be connected to automatic valves 620 and 622, and the differential pressure transducer 606 may be connected to valves 624 and 626. For example, if the first differential pressure transducer 602 detects an overpressure condition, the automatic valve 616 connected to the upstream pressure source may be automatically opened to connect the negative side of the transducer 602 to the upstream pressure source. The automatic valve 618 may be automatically closed to isolate the transducer 602 to the downstream pressure source, such that both sides of the transducer 602 are opened to the upstream pressure source and the differential pressure will be zero to protect the transducer. The automatic valve 622 may be automatically opened such that the second differential pressure transducer 604 having the greater pressure range may be engaged to measure the differential pressure. The automatic valves 620, 622, 624, and 626 may thus operate in a similar manner to protect the valves 604 and 606 from overpressure conditions and engage the third differential pressure transducer 606 to measure the differential pressure.

Density and Viscosity Measurement System

Figure 7:
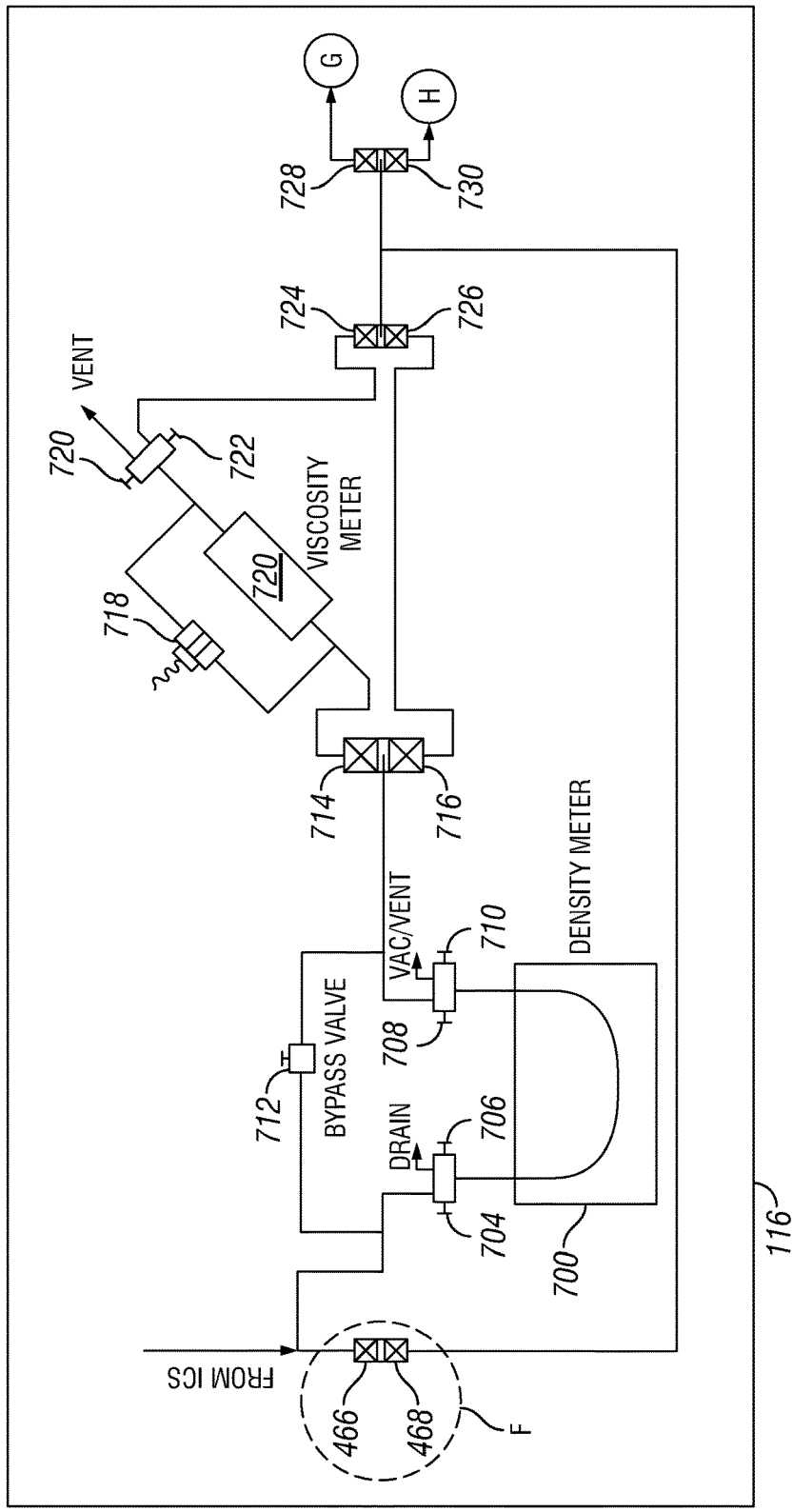
FIG. 7 is a schematic diagram of the density and viscosity measurement system of the dual core flooding apparatus of FIG. 1 in accordance with an embodiment of the disclosure.

FIG. 7 depicts a schematic diagram of the density and viscosity measurement system 116 in accordance with an example embodiment of the disclosure. The density and viscosity measurement system 116 may be connected to the first core holder 102 via the automatic valves 466 and 468, as shown by connection block F in FIGS. 4A-4D and FIG. 7. The density and viscosity measurement system 116 may include a density meter 700 and a viscosity meter 702. The density meter 700 may be connected to valves 704 and 706 and valves 708 and 710. In some embodiments, the density meter 700 may be an mPDS 2000V3 Evaluation Unit and a DMA 512P/DMA HPM external Density Cell manufactured by Anon-Paar USA Inc., of Ashland, Va., USA. In some embodiments, the density meter 700 may have a maximum working pressure of about 20,000 psi, a temperature range of about $-10°$ C. to about $200°$ C., a measurement range of about 0 $g/cm^3$ to about 3 $g/cm^3$, and an accuracy of about 0.0001 $g/cm^3$.

In some embodiments, the valves 704 and 706 and the valves 708 and 710 may be manual valves. The density and viscosity measurement system 116 may also include a bypass valve 712 to enable bypassing the density meter 700. The valve 708 may be connected to the automatic valves 714 and 716. In some embodiments, the valves 714 and 716 are automatic valves.

The viscosity meter 702 may be connected to the automatic valve 714. The density and viscosity measurement system 116 may include a differential pressure transducer 718 to measure differential pressure across the viscosity meter 702. The outlet from the viscosity meter may be coupled to the valves 720 and 722. In some embodiments, the viscosity meter 702 may be a Cambridge Viscosity viscosity meter manufactured by PAC of Houston, Tex., USA.

The density and viscosity measurement system 116 may include an arrangement of valves to direct the fluids exiting the density meter 700, the viscosity meter 702, and the bypass. For example, as shown in FIG. 7, the density and viscosity measurement system 116 may include automatic valves 724 and 726 and automatic valves 728 and 730. The outlet from the automatic valve 728 may be connected to the first back pressure regulation system 120, as shown by connection block G in FIGS. 7 and 10, and the outlet from the automatic valve 730 may be connected to the first oil/water separation system 118, as shown by connection block H in FIGS. 7 and 8. The valve 468 may provide for a bypass of the density meter 700 and the viscosity meter 702. The automatic valves 716 and 726 may provide for a bypass of the viscosity meter 702.

To measure density, viscosity, or both, fluid may be routed from the first core holder 102 or the second core holder 104 through the valve 466, through the valve 704, and to the density meter 700. Fluid exiting the density meter 700 may be routed through the valve 708 to the automatic valve 714 to the viscosity meter 702. The fluid exiting the viscosity meter 702 may be routed through the valve 722, through the automatic valve 724, and through the automatic valve 728 to the first back pressure regulation system 120 (as shown by connection block G) and through the automatic valve 730 to the first oil/water separation system 118 (as shown by connection block H).

Oil/Water Separators

Figure 8:
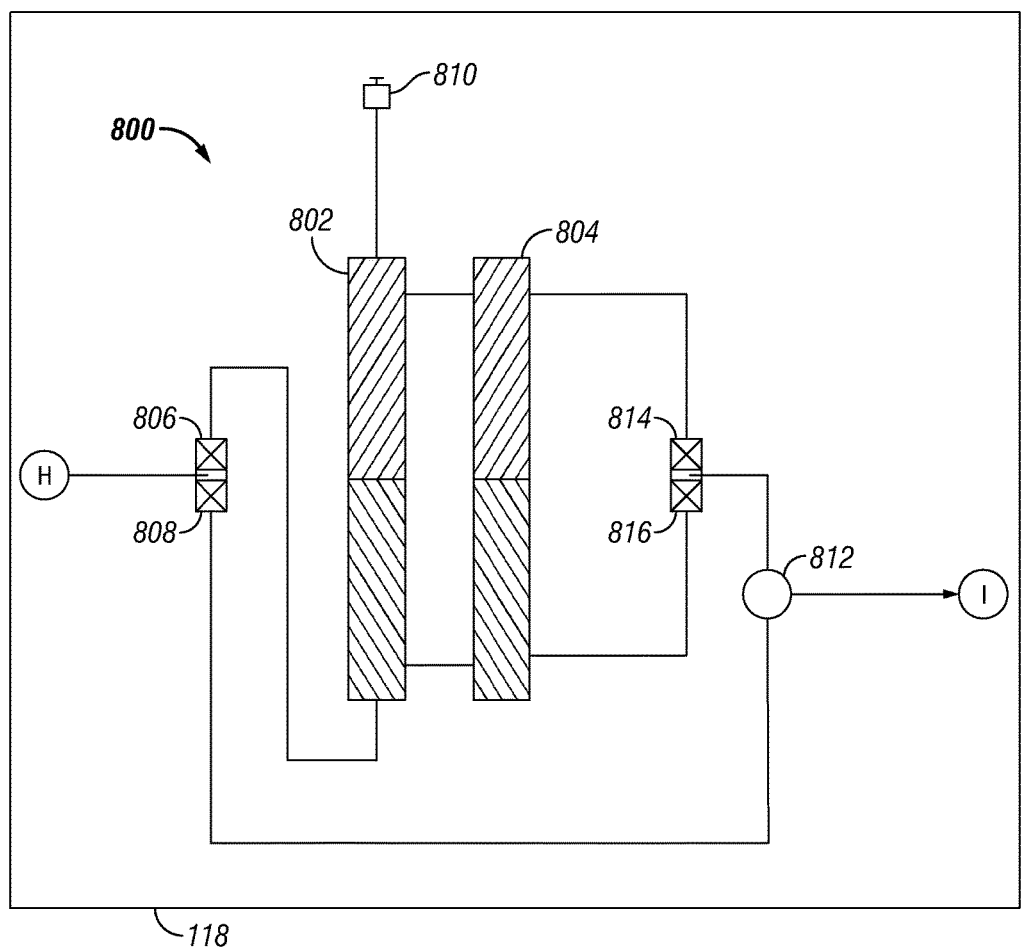
FIG. 8 is a schematic diagram of a first oil/water separation system of the dual core flooding apparatus of FIG. 1 in accordance with an embodiment of the disclosure.

FIG. 8 is a schematic diagram of the first oil/water separation system 118 in accordance with an example embodiment of the disclosure. The first oil/water separation system 118 may be used to separate oil and water in fluid from the first core holder 102 for subsequent measurement of the oil and water. In some embodiments, the first oil/water separation system 118 includes a gravity-based two-phase high pressure separator 800 having a first phase 802 and a second phase 804. In some embodiments, the separator 800 may be an SFS-032 two phase sonic fluid separator manufactured by Coretest Systems, Inc., of Morgan Hill, Calif., USA. In some embodiments, the separator 800 may have a maximum working pressure of about 10,000 psi, a maximum temperature of about 150° C., a total volume of about 4900 ml, a maximum change of water volume of about 200 ml, a maximum change of oil volume of about 200 ml, a bore diameter of about 25.4 mm, and a bore length of about 384.82 mm.

As shown in FIGS. 7 and 8 and connection block H, the first oil/water separation system 118 may be connected to the density and viscosity measurement system 116. The automatic valve 730 of the density and viscosity measurement system 116 may be connected to valves 806 and 808 shown in FIG. 8. In some embodiments, the automatic valves 806 and 808 are automatic valves. The automatic valve 806 may be connected to the first phase 802 of the separator 800. In some embodiments, the first phase 802 of the separator 800 may be connected to valve 810. In some embodiments, valve 810 is a stainless steel valve. The automatic valve 808 may provide as a bypass to the separator 800 and may be coupled to connector 812 at the output of the first oil/water separation system 118.

The outlet from the separator 800 may be coupled to automatic valves 814 and 816. For example, one separated phase may be output via automatic valve 814, and the other separated phase may be output via automatic valve 816. The outlets from automatic valves 814 and 816 may be connected to the connector 812, and the output from the connector 812 may be provided to the first back pressure regulation system 120, as shown by connection block I in FIGS. 8 and 10.

The fluid from the density and viscosity measurement system 116 (or the bypass of the system 116) may be routed to the automatic valve 806 and the first phase 802 of the oil/water separator 800. In some embodiments, the separator 800 may automatically measure the high of the oil column. Separated water from the bottom of the separator 800 may be routed through the automatic valve 816, through the connector 812, and to the first back pressure regulation system 120 for measurement by a balance described further in the disclosure. In some embodiments, the effluent measurement system 122 may be used to measure oil and water production; in such embodiments, the fluid may be routed through the automatic valve 808 to bypass the separator 800 and be provided directly to the first back pressure regulation system 120, as shown by connection block I in FIGS. 8 and 10.

Figure 9:
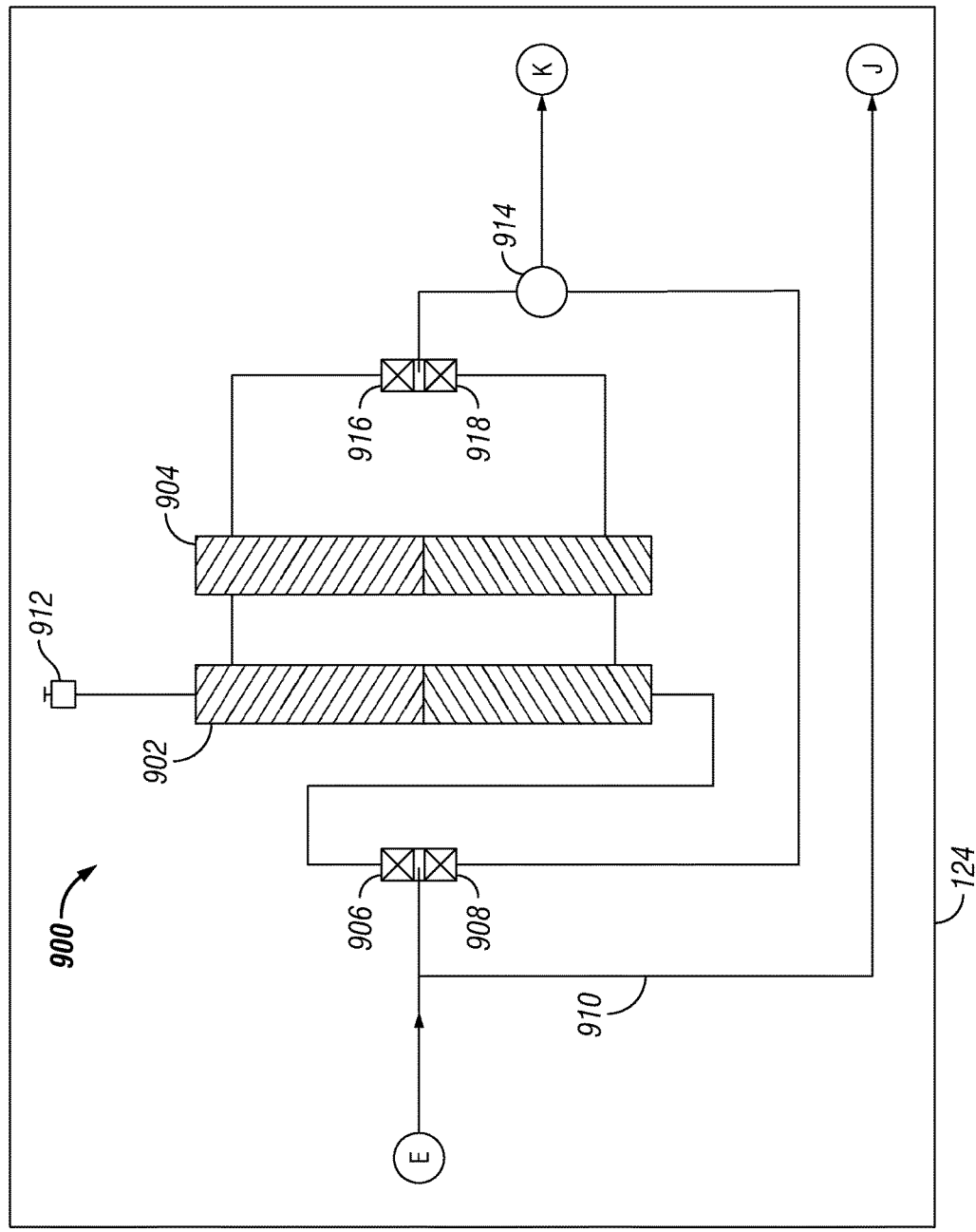
FIG. 9 is a schematic diagram of a second oil/water separation system of the dual core flooding apparatus of FIG. 1 in accordance with an embodiment of the disclosure.

FIG. 9 depicts a schematic diagram of the second oil/water separation system 124 in accordance with an example embodiment of the disclosure. In some embodiments, the second oil/water separation system 124 may be similar to the first oil/water separation system 118 and may include a gravity-based two-phase high pressure separator 900 having a first phase 902 and a second phase 904. The second oil/water separation system 124 may be used to separate oil and water in fluid from the second core holder 104 for subsequent measurement of the oil and water. In some embodiments, the second oil/water separation system 124 includes a gravity-based two-phase high pressure separator 900 having a first phase 902 and a second phase 904. In some embodiments, the separator 900 may be an SFS-032 two phase sonic fluid separator manufactured by Coretest Systems, Inc., of Morgan Hill, Calif., USA.

As shown in FIG. 9 and FIGS. 4A-4D by connection block E, the second oil/water separator may be connected to the second core holder 104. The outlet from the second core holder 104 may be connected to automatic valves 906 and 908 shown in FIG. 9. In some embodiments, the valves 906 and 908 are automatic valves. In some embodiments, some of the output from the second core holder 104 may be provided to the second back pressure regulation system 126, as shown by line 910 and connection block J in FIGS. 9 and 10. The automatic valve 906 may be connected to the first phase 902 of the separator 900. In some embodiments, the first phase 902 of the separator may be connected to valve 912. In some embodiments, the valve 912 is a stainless steel valve. The valve 908 may provide a bypass to the separator 900 and may be connected to connector 914 at the output of the second oil/water separation system 124.

The outlet from the separator 900 may be coupled to automatic valves 916 and 918. For example, one separated phase may be output via automatic valve 916, and the other separated phase may be output via automatic valve 918. In some embodiments, the valves 916 and 918 may be automatic valves. The outlets from automatic valves 916 and 918 may be connected to the connector 914, and the output from the connector 914 may be provided to the second back pressure regulation system 126, as shown by connection block K in FIGS. 9 and 10.

A portion of the fluid from the second core holder 104 may be routed to the valve 906 and the first phase 902 of the oil water separator. Another portion of the fluid from the second core holder 104 may be routed directly to the second back pressure regulation system 126, as shown by connection block J in FIGS. 9 and 10. In some embodiments, the separator 900 may automatically measure the height of the oil column. Separated water from the bottom of the separator 900 may be routed through the automatic valve 918, through the connector 914, and to the second back pressure regulation system 126 for measurement by a balance described further in the disclosure. In some embodiments, the second effluent measurement system 128 may be used to measure oil and water production; in such embodiments, the fluid may be routed through the valve 908 to bypass the separator 900 and be provided directly to the second back pressure regulation system 126 (as shown by connection block K).

Back Pressure Regulation Systems

Figure 10:
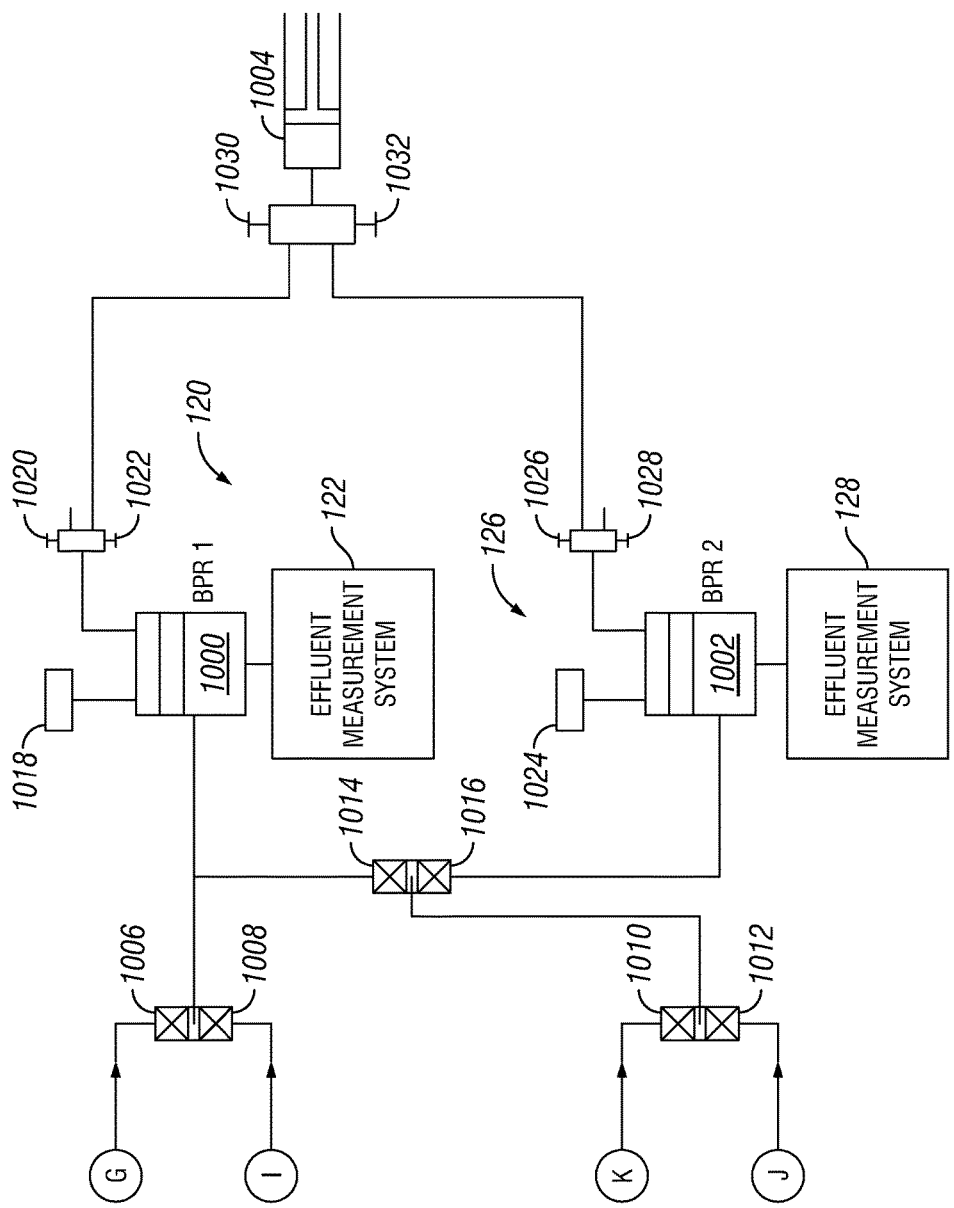
FIG. 10 is a schematic diagram of a first back pressure regulation system and a second back pressure regulation system of the dual core flooding apparatus of FIG. 1 in accordance with an embodiment of the disclosure.

FIG. 10 is a schematic diagram of the first back pressure regulation system 120 and the second back pressure regulation system 126 in accordance with an example embodiment of the disclosure. The first back pressure regulation system 120 and the second back pressure regulation system 126 (collectively referred to as the "dual back pressure regulation system") may establish and control the pore pressure of core plugs in the first core holder 102 and the second core holder 104 during core flooding and other tests.

As shown in FIG. 10, the first back pressure system 120 may include a first back pressure regulator 1000 and the second back pressure system 126 may include a second back pressure regulator 1002. Both the back pressure regulators 1000 and 1002 may be controlled by a back pressure regulator control system 1004. In some embodiments, the back pressure regulation control system 1004 may be manufactured by Coretest Systems, Inc., of Morgan Hill, Calif., USA.

The input to and output from the back pressure regulators 1000 and 1002 may be controlled by an arrangement of valves and other components. For example, as shown in FIG. 10 and by connection block G in FIGS. 7 and 10, automatic valve 1006 may be connected to the density and viscosity measurement system 116. Similarly, as shown by connection block I in FIGS. 8 and 10, the automatic valve 1008 may be connected to the first oil/water separation system 118. In some embodiments, the automatic valves 1006 and 1008 are automatic valves. As also shown in FIGS. 9 and 10 by connection block K, the automatic valve 1010 may be connected to the second oil/water separator 124. Additionally, as shown by connection block J in FIGS. 9 and 10, the automatic valve 1012 may be connected to the second core holder 104. In some embodiments, the automatic valves 1010 and 1012 are automatic valves. The automatic valves 1006 and 1008 may be connected to automatic valve 1014, and the automatic valves 1010 and 1012 may be connected to the automatic valve 1016. The first back pressure regulator 1000 may be connected to the automatic valves 1006 and 1008. The first back pressure regulation system 120 may also include a Heise® gauge 1018 connected to the first back pressure regulator 1000. The Heise® gauge 1018 may measure the expectant value of back pressure applied by the first back pressure regulator 1000. The first back pressure regulator 1000 may be connected to the first effluent measurement system 122. The first back pressure regulator 1000 may be connected to valves 1020 and 1022. In some embodiments, the valves 1020 and 1022 are manual valves.

The second back pressure regulator 1002 may be connected to the automatic valve 1016. The second back pressure regulation system 126 may also include a Heise® gauge 1024 connected to the second back pressure regulator 1002. The Heise® gauge 1024 may measure the expectant value of back pressure applied by the second back pressure regulator 1002. The second back pressure regulator 1002 may also be connected to valves 1026 and 1028. In some embodiments, the valves 1026 and 1028 are manual valves. The second back pressure regulator 1002 may also be connected to the first effluent measurement system 128.

The back pressure regulator control system 1004 may be connected to valves 1030 and 1032. In some embodiments, the valves 1030 and 1032 may be manual valves. As shown in FIG. 10, the back pressure regulator control system 1004 may be connected to the first back pressure regulator 1000 via the valves 1030 and 1022. As also shown in FIG. 10, the back pressure regulator control system 1004 may be connected to the second back pressure regulator 1002 via the valves 1032 and 1026. In some embodiments, the back pressure regulation control system 1004 may be manufactured by Coretest Systems, Inc., of Morgan Hill, Calif., USA. In some embodiments, the back pressure regulation control system 1004 may have a maximum working pressure of about 10,000 psi.

The first back pressure regulation system 120 may be used to set an expectant value of back pressure before running core flooding tests. Produced fluid from the core plug in the first core holder 102 is routed through the automatic valve 1006 or the automatic valve 1008 against an expectant pressure applied by the first back pressure regulator 1000 such that pressure builds up in the core plug in the first core holder 102 by the fluids delivery system 106. If the fluid pressure is greater than the expectant pressure applied by the back pressure regulator 1000, the fluid produced from the core plug in the first core holder 102 is routed through the back pressure regulator 1000 to the first effluent measurement system 122 and to a balance or fraction collector.

The second back pressure regulation system 126 may be used to set an expectant value of back pressure for the core plug in the second core holder 104 before running core flooding tests. Produced fluid from the core plug in the second core holder 104 is routed through the automatic valve 1010 or the valve 1012 against an expectant pressure applied by the second back pressure regulator 1004 such that pressure builds up in the core plug in the second core holder 104 by the fluids delivery system 106. If the fluid pressure is greater than the expectant pressure applied by the back pressure regulator 1004, the fluid produced from the core plug in the second core holder 104 is routed through the back pressure regulator 1004 to the second effluent measurement system 128 and to a balance or fraction collector.

Automated Confining Pressure System

Figure 11:
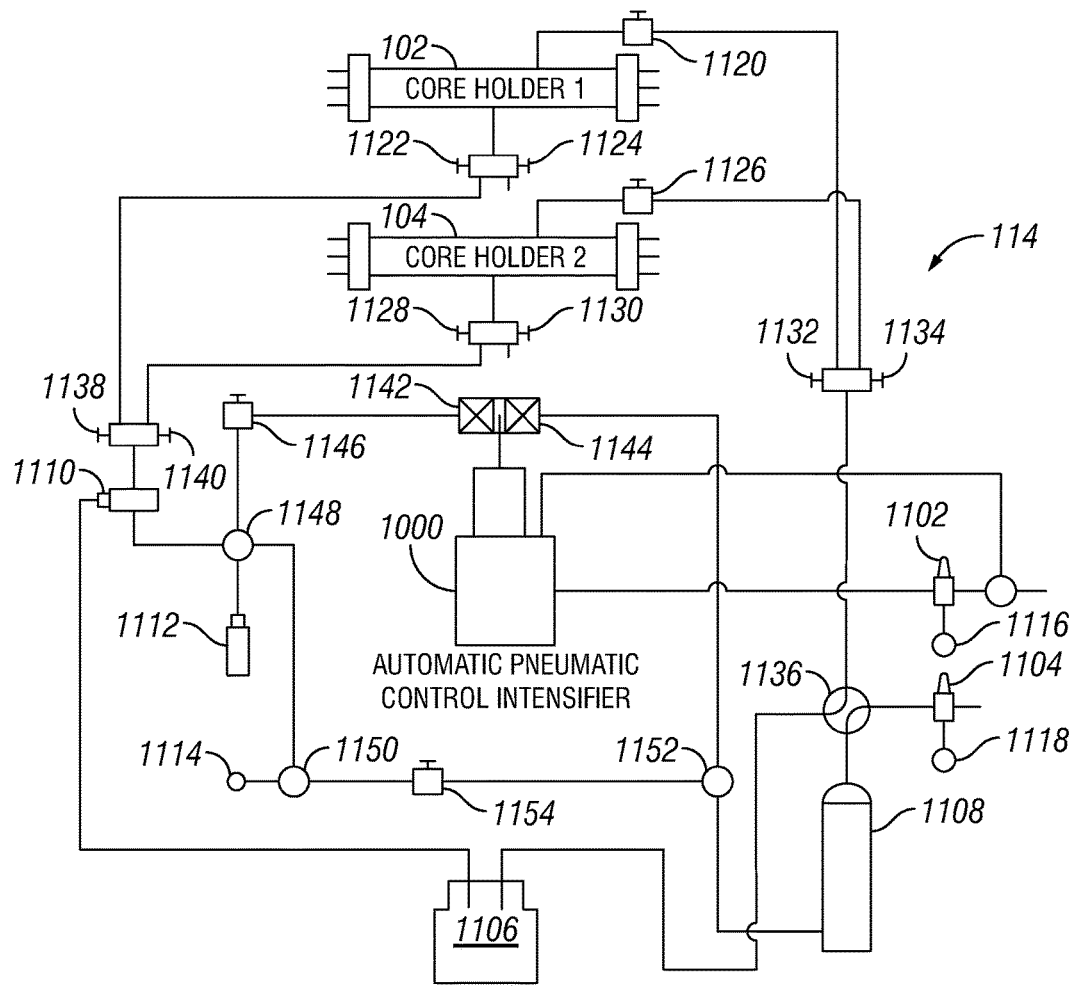
FIG. 11 is a schematic diagram of an automated confining pressure system of the dual core flooding apparatus of FIG. 1 in accordance with an embodiment of the disclosure.

FIG. 11 is a schematic diagram of the automated confining pressure system 114 in accordance with an example embodiment of the disclosure. The automated confining pressure system 114 may include an automatic pneumatic control intensifier (PCI) 1100, air regulators 1102 and 1104, a drain reservoir 1106, a water reservoir 1108 (for example, a deionized water reservoir), an overpressure burst disk 1110, a pressure transducer 1112, and gauges 1114, 1116, and 1118. In some embodiments, the automated confining pressure system 114 may be manufactured by Coretest Systems, Inc., of Morgan Hill, Calif., USA.

The automated confining pressure system 114 and components thereof may be connected to the first core holder 102 and the second core holder 104 via an arrangement of valves. For example, as shown in FIG. 11, first core holder may be connected to valves 1120, 1122, and 1124. In some embodiments, the valve 1120 may be a stainless steel valve. In some embodiments, the valves 1122 and 1124 may be manual valves. As also shown in FIG. 11, the second core holder 104 may be connected to valves 1126, 1128, and 1130. In some embodiments, the valve 1126 may be a stainless steel valve. In some embodiments, the valves 1128 and 1130 may be manual valves.

The valve 1120 may be connected to valve 1132, and the valve 1126 may be connected to valve 1134. In some embodiments, the valves 1132 and 1134 are manual valves. The valves 1132 and 1134 may be connected to the drain reservoir 1106 via connector 1136.

The valve 1122 may connected to valve 1138, and the valve 1128 may be connected to valve 1140. In some embodiments, the valves 1138 and 1140 are connected to the overpressure burst disk 1110. In some embodiments, the overpressure burst disk 1110 may be a 6000 psi burst disk. The automatic pneumatic control intensifier 1100 may be connected to automatic valves 1142 and 1144. In some embodiments, the valves 1142 and 1144 may be automatic valves. The automatic valve 1142 may be connected to the valve 1146. In some embodiments, the valve 1146 may be a stainless steel valve. The automatic pneumatic control intensifier 1100 the transducer 1112, the water reservoir 1108 and other components may be connected via the connectors 1148, 1150, and 1152, and the valve 1154, as shown in FIG. 11. In some embodiments, the valve 154 may be a manual valve.

The automatic pneumatic control intensifier 1100 may have a multiplication in the range of 100:1 with a minimum required air pressure of 80 psi. The automatic pneumatic control intensifier 1100 may have a drive pressure in the range of 0 psi to 100 psi and an outlet pressure in the range of 400 psi to 10000 psi for confining pressure. To set the confining pressure in the first core holder 102, the valve 1138 and the valve 1122 may be used to connect the automated confining pressure system 114 to the first core holder 102. To set the confining pressure in the second core holder 104, the valve 1140 and the valve 1128 may be used to connect the automated confining pressure system 114 to the second core holder 104. The confining pressure of the first core holder 102 and the second core holder 104 may be set independently and simultaneously.

Effluent Measurement Systems

Figure 12:
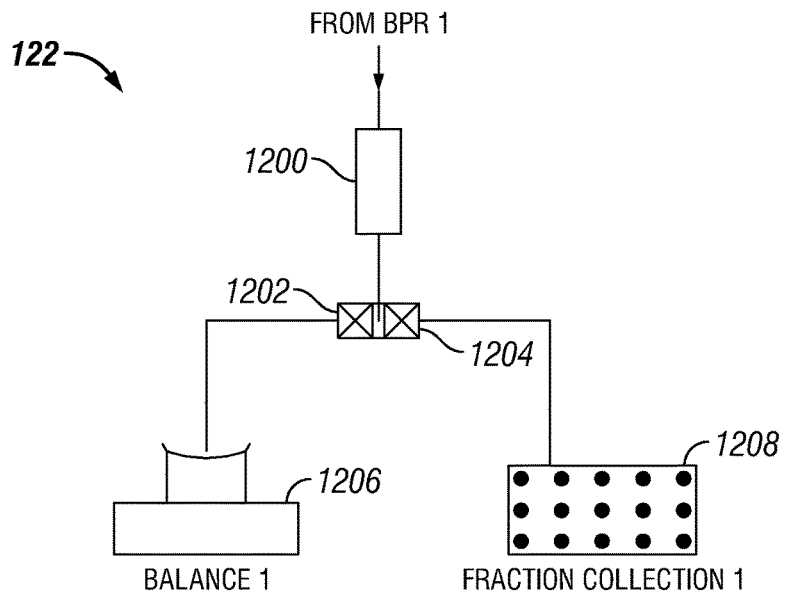
FIG. 12 is a schematic diagram of a first effluent measurement system of the dual core flooding apparatus of FIG. 1 in accordance with an embodiment of the disclosure.

FIG. 12 is a schematic diagram of the first effluent measurement system 122 in accordance with an example embodiment of the disclosure. The first effluent measurement system 122 may include a gas meter 1200, automatic valves 1202 and 1204, a balance 1206, and a fraction collector 1208. The produced effluents from the first core holder 102 may be routed through the first back pressure regulator 1000 to the first effluent measurement system 122. The produced effluents may be routed through the automatic valve 1204 to the fraction collector 1208. For example, if a liquid/gas displacement test is performed, such as by displacing oil by $CO_2$, the fraction collector 1208 may be used to measure the produced liquid and the gas meter 1200 may measure produced gas. If the balance is used to measure effluent production, the produced effluents may be routed through the automatic valve 1202 to the balance 1206 and the automatic valve 1204 may be closed.

Figure 13:
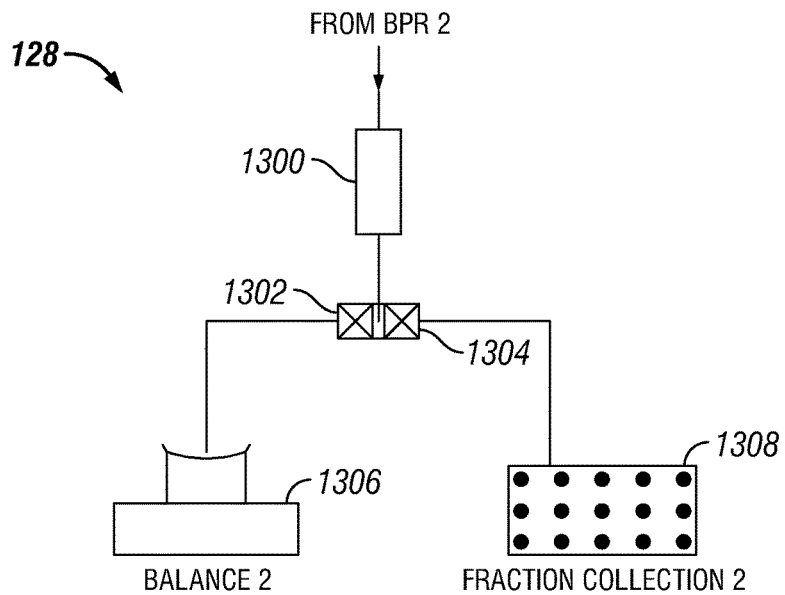
FIG. 13 is a schematic diagram of a second effluent measurement system of the dual core flooding apparatus of FIG. 1 in accordance with an embodiment of the disclosure.

FIG. 13 depicts a schematic diagram of the second effluent measurement system 128 in accordance with an example embodiment of the disclosure. The second effluent measurement system 128 may include a gas meter 1300, automatic valves 1302 and 1304, a balance 1306, and a fraction collector 1308. The produced effluents from the second core holder 104 may be routed through the second back pressure regulator 1004 to the second effluent measurement system 128. The produced effluents may be routed through the automatic valve 1302 to the fraction collector 1308. For example, if a liquid/gas displacement test is performed, such as by displacing oil by $CO_2$, the fraction collector 1308 may be used to measure the produced liquid and the gas meter 1300 may measure produced gas. If the balance is used to measure effluent production, the produced effluents may be routed through the automatic valve 1302 to the balance 1306 and the automatic valve 1304 may be closed.

Image Capture System and Core Holder Bypass

Figure 14:
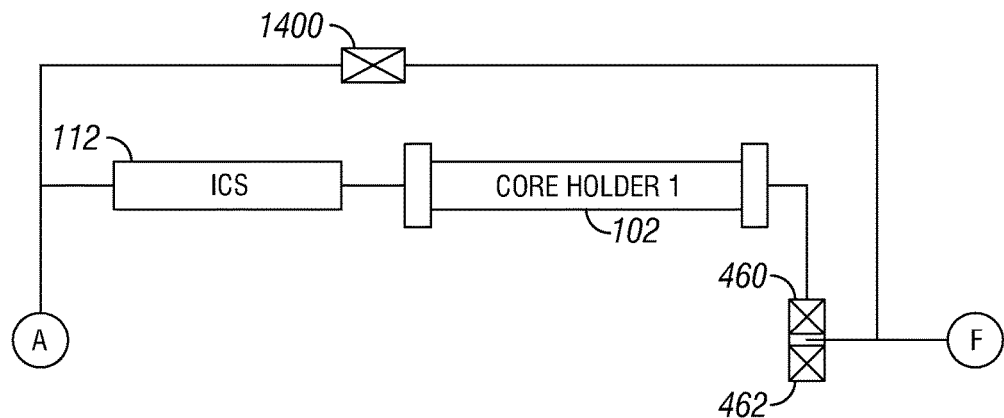
FIG. 14 is a schematic diagram of a bypass of an image capture system and a first core holder of the dual core flooding apparatus of FIG. 1 in accordance with an embodiment of the disclosure.

In some embodiments, the initial properties of an injection fluid may be measured before injection into a core plug in a core holder. FIG. 14 is a schematic diagram of the bypass of the image capture system 112 and the first core holder 102 to enable measurement of the initial properties of an injection fluid in accordance with an example embodiment of the disclosure. As shown by connection block A in FIG. 14 and FIGS. 2A-2D, fluid may be routed from the fluids delivery system 106 to the automatic valve 254 and to the bypass valve 1400. Fluid may then be routed via the bypass valve 1400 to the density and viscosity measurement system 116, as shown by connection block F in FIGS. 7 and 14. The initial properties of the fluid may thus be measured by the density and viscosity measurement system 116 after bypassing the image capture system 116 and the first core holder 102. The valve 720 shown in FIG. 7 and discussed supra may be a drain valve for the bypassed fluid. In some embodiments, the initial property of the injection fluid may be measured at a specific pressure by connecting the first back pressure regulation system 120 to the valve 720.

Data Acquisition System and Control System

Figure 15:
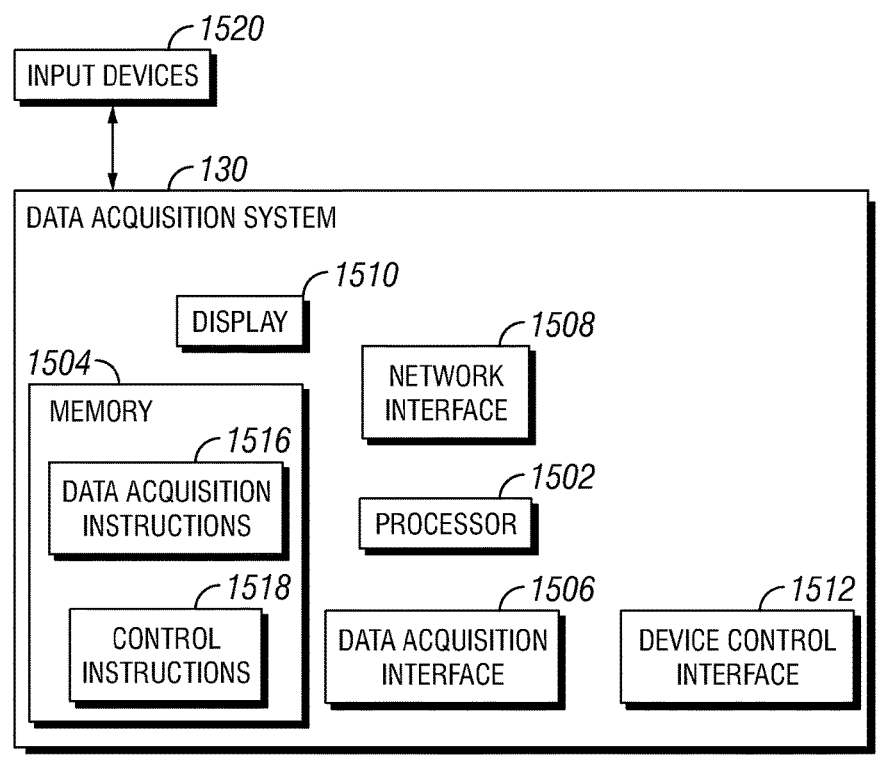
FIG. 15 is a block diagram of a data acquisition and control system of the dual core flooding apparatus of FIG. 1 in accordance with an embodiment of the disclosure.

FIG. 15 depicts a block diagram of the data acquisition and control system 130 in accordance with an example embodiment of the disclosure. The data acquisition system 130 may include a data acquisition and control processor 1502, a memory 1504, a data acquisition interface 1506, and a device control interface 1512. In some embodiments, the data acquisition system 130 may also include a network interface 1508. In some embodiments, the data acquisition and control system 130 may include a personal computer, such as a desktop computer, a laptop computer, a tablet computer, or the like.

The data acquisition system 130 may acquire data from various components of the dual core flooding apparatus 100, such as the fluids delivery system 106, the image capture system 112, the differential pressure measurement systems 108 and 110, the density and viscosity measurement system 116, the oil/water separators 118 and 124, the back pressure regulation systems 120 and 126, and the automated confining pressure system 114. In some embodiments, the data acquisition system 130 may include a personal computer, such as a desktop computer, a laptop computer, a tablet computer, or the like.

The data acquisition and control processor 1502 (as used the disclosure, the term "processor" encompasses microprocessors) may include one or more processors having the capability to receive and process data from sensors of the data acquisition system 130. In some embodiments, the processor 1502 may include an application-specific integrated circuit (AISC). In some embodiments, the data acquisition processor 1502 may include a reduced instruction set (RISC) processor. Additionally, the processor 1502 may include a single-core processors and multicore processors and may include graphics processors. Multiple processors may be employed to provide for parallel or sequential execution of one or more of the techniques described in the disclosure. In some embodiments, the processor 1502 may include, for example, a first data acquisition processor for data acquisition functions and a control processor for control functions. The processor 1502 may receive instructions and data from a memory (for example, memory 1504).

The memory 1504 (which may include one or more tangible non-transitory computer readable storage mediums) of the data acquisition system 130 may include volatile memory, such as random access memory (RAM), and non-volatile memory, such as ROM, flash memory, a hard drive, any other suitable optical, magnetic, or solid-state storage medium, or a combination thereof. The memory 1504 may be accessible by the processor 1502 and may store executable computer code. The executable computer code may include computer program instructions for implementing one or more techniques described in the disclosure, For example, the executable computer code may include data acquisition instructions 1516 executable by a processor (for example, the processor 1502) to implement one or more embodiments of the present disclosure. In some embodiments, the data acquisition instructions 1516 may include instructions for acquiring data from sensors of the data acquisition system 130 via the data acquisition interface 1506 and processing the acquired data (for example, converting the data from analog data to digital data). In some embodiments, the processing may include comparing an acquired data value (for example, a pressure value) to a threshold value and providing a notification based on the comparison.

In another example, the executable computer code may include dual core apparatus control instructions 1518. For example, the dual core flooding apparatus control instructions 1518 may include instruction for controlling the fluids delivery system 106, the image capture system 112, the differential pressure measurement systems 108 and 110, the density and viscosity measurement system 116, the oil/water separators 118 and 124, the back pressure regulation systems 120 and 126, the automated confining pressure system 114, or any combination thereof, in the manner described in the disclosure to analyze the flow status of core plugs in the core holder 102, core holder 104, or both. Such instructions may include instruction to send control signals to, for example, valves of the dual core flooding apparatus 100, to pumps of the dual core flooding apparatus 100, the back pressure regulation system 1004, the automatic pneumatic control intensifier 1100, and other components described in the disclosure. In some embodiments, the processing may include comparing a data value (for example, a pressure value) to a threshold value and providing a notification based on the comparison. In some embodiments, the processing may include comparing a data value (for example, a pressure value) to a threshold value and performing an action (for example, closing one or more valves, changing the speed of a pump, and so on) based on the comparison.

The data acquisition interface 1506 (which may include one or more interfaces) may provide for communication between the data acquisition system 130 and components (for example, sensors) of the dual core flooding apparatus 100. For example, the data acquisition interface 1506 may include circuitry for communication with pressure transducers, the camera 306, the density meter 700, the viscosity meter 702, the separators 800 and 900, the back pressure regulators 1000 and 1004, and other components of the dual core flooding apparatus 100. The data acquisition interface 1506 may include a wired interface or a wireless interface and may for communication over wired networks or wireless networks. In some embodiments, the data acquisition interface 1506 may enable communication over industrial control networks. The data acquisition interface 1506 may provide for communication using suitable standards, protocols, and technologies, such as serial communication protocols (for example, Modbus), Industrial Ethernet (IE), the Common Industrial Protocol (CIP), and the like.

The network interface 1508 may provide for communication between the data acquisition system 130 and other devices, such as the control system 1500. In some embodiments, the network interface 1506 and data acquisition interface 1506 may be combined. The network interface 1508 may include a wired network interface card (NIC), a wireless (for example, radio frequency) network interface card, or combination thereof. The network interface 1508 may include circuitry for receiving and sending signals to and from communications networks, such as an antenna system, an RF transceiver, an amplifier, a tuner, an oscillator, a digital signal processor, and so forth. The network interface 1508 may communicate with networks (for example, network 504), such as the Internet, an intranet, a wide area network (WAN), a local area network (LAN), a metropolitan area network (MAN) or other networks. Communication over networks may use suitable standards, protocols, and technologies, such as Ethernet Bluetooth, Wireless Fidelity (Wi-Fi) (for example, IEEE 802.11 standards), and other standards, protocols, and technologies. In some embodiments, the network interface 1508 may enable communication over industrial control networks.

The display 1510 may include a cathode ray tube (CRT) display, liquid crystal display (LCD), an organic light emitting diode (OLED) display, or other suitable display. The display 1510 may display a user interface (for example, a graphical user interface) that may display data acquired from components of the received from the dual core flooding apparatus 100. In accordance with some embodiments, the display 1510 may be a touch screen and may include or be provided with touch sensitive elements through which a user may interact with the user interface. In some embodiments, the display 1510 may display a notification, such as alert, if data received from the components of the dual core flooding apparatus 100 meet a condition. For example, a notification may be displayed if a pressure value acquired from a pressure transducer exceeds a threshold value.

The data acquisition and control system 130 may also provide control signals to components of the dual core flooding apparatus 100. For example, the data acquisition and control system 130 may provide control signals to the fluids delivery system 106, the image capture system 112, the differential pressure measurement systems 108 and 110, the density and viscosity measurement system 116, the oil/water separators 118 and 124, the back pressure regulation systems 120 and 126, the automated confining pressure system 114, or any combination thereof.

The device control interface 1512 (which may include one or more interfaces) may provide for communication between the data acquisition system 130 and controllable devices (for example, valves, pumps, and the like) of the dual core flooding apparatus 100. For example, the device control interface 1512 may include circuitry for sending control signals to valves, pumps, the camera 306, automated confining pressure system 114, the back pressure regulation control system 1004 and other devices of the dual core flooding apparatus 100. The device control interface 1512 may include a wired interface or a wireless interface and may for communication over wired networks or wireless networks. In some embodiments, the device control interface 1512 may enable communication over industrial control networks. The device control interface 1512 may provide for communication using suitable standards, protocols, and technologies, such as serial communication protocols (for example, Modbus), Industrial Ethernet (IE), the Common Industrial Protocol (CIP), and the like.

In some embodiments, the data acquisition and control system 130 may be coupled to an input device 1520 (for example, one or more input devices). The input devices 1520 may include, for example, a keyboard, a mouse, a microphone, or other input devices. In some embodiments, the input device 1520 may enable interaction with a user interface displayed on the display 1510. For example, in some embodiments, the input devices 1520 may provide for the input of values (for example, pressure values, flow rates, and the like) to directly or indirectly control components of the dual core flooding apparatus 100.

Alternatively, in some embodiments, the data acquisition and control system 130 may be implemented in multiple systems or devices, such that data acquisition functions are performed by a first system or device and control functions are performed by a second system or device. Such separated systems or devices may have similar components to the data acquisition system 130. In some embodiments, the data acquisition system 130 may be a part of an industrial control system (such as a Supervisory Control and Data Acquisition System (SCADA)), a distributed control system (DSC) or other similar systems.

Examples

The following examples are included to demonstrate embodiments of the disclosure. It should be appreciated by those of skill in the art that the techniques and compositions disclosed in the example which follows represents techniques and compositions discovered to function well in the practice of the disclosure, and thus can be considered to constitute modes for its practice. However, those of skill in the art should, in light of the present disclosure, appreciate that many changes can be made in the specific embodiments which are disclosed and still obtain a like or a similar result without departing from the spirit and scope of the disclosure.

In some embodiments, the dual core flooding apparatus 100 may be used to investigate different oil recovery techniques, including secondary and tertiary oil recovery processes. For example, oil recovery during water and CO2 into a heterogeneous reservoir may be limited as a result of an early breakthrough of water and CO2 caused by viscous fingering and gravity override such that poor displacement efficiencies occurs. Accordingly, in some embodiments, the dual core flooding apparatus 100 may be used to study the impact of reservoir heterogeneity on oil recovery by seawater and CO2 flooding by, for example, seawater and CO2 injections, thermal foam slug injections, and post-seawater and post-CO2 injections. In the core flooding tests described infra, live oil, dead crude oil, seawater, and supercritical CO2 were used. The core flooding tests were conducted at a temperature of 212° F., a pore pressure of 3200 psi, and a confining pressure of 4500 psi.

In the example experiment, two core plugs were selected: a high permeable core plug (HPCP) and a low permeable core plug (LPCP). The core plugs were prepared by saturating the core plugs with brine (for example, to determine the pore volume of the core plug), performing brine permeability measurements, and then establishing initial water and original oil saturation of the core plugs. The high permeable core plug with initial water and original oil may be placed in to the first core holder 102, and the low permeable core plug with initial water and original oil were placed in the second core holder 104. Deionized water was filled in into the annulus between a rubber sleeve and the core holders 102 and 104 via the automated confining pressure system 114 at ambient conditions. All fluid lines (for example, inlet lines, outlines, pressure lines, and bypass lines) were connected to the core holders 102 and 104, as shown in FIG. 4.

The automated confining pressure system was used to apply a confining pressure of 1500 psi to both core holders 102 and 104. The back pressure regulation systems 120 and 126 were used to establish a pore pressure of 500 psi of the core plugs in core holders 102 and 104 respectively. The pore pressure was established by injecting dead crude oil at a flowrate of 1.0 cc/min at ambient temperatures using the first pump 206. The pore pressure of the high permeable core plug in the first core holder 102 was established by injecting the dead crude oil using the fluids delivery system 106 shown in FIG. 2A and routed via the following components: the first pump 206, the valves 208 and 213, the connector 217, the valves 219 and 225, the accumulator 203, the valve 238, the connector 236, the automatic valve 253, and the automatic valve 254. The dead crude oil was routed to bypass the image capture system 112 shown in FIG. 3 via the valve 302 and the valve 318. The dead crude oil was then routed to the high permeable core plug via the inlet of the first core holder 102 shown in FIG. 4A via the automatic valve 320 and the valve 410. The dead crude oil was routed from the outlet of the first core holder shown in FIG. 4A via the automatic valve 460 and the valve 466 to the density and viscosity measurement system 116. The dead crude oil was routed to bypass the density meter 700 and the viscosity meter 702 via the valve 712, the automatic valve 716, the automatic valve 726, and the automatic valve 728 shown in FIG. 7. The dead crude oil was then routed to the first back pressure regulator 1000 via the valve 1006 shown in FIG. 10 to first establish a pore pressure of 500 psi. After establishing a pore pressure of 500 psi, a confining pressure of 2000 psi was established using the automating confining pressure system 114 and a pore pressure of 1000 psi was established using the back pressure regulator 1000. After establishing a confining pressure of 2000 psi and a pore pressure of 1000 psi, the confining pressure and pore pressure were increased in increments of 500 psi until a confining pressure of 4500 psi and a pore pressure of 3200 psi were established.

The pore pressure of the low permeable core plug in the second core holder 104 was established by injecting the dead crude oil using the fluids delivery system 106 shown in FIG. 2A and the same routing path described supra to the automatic valves 254 and 255. After establishing the confining pressure and pore pressure for the high permeable core plug in the first core holder 102, the automatic valve 254 was closed and the confining pressure and pore pressure for the low permeable core plug in the second core holder 104 were established by increasing the confining pressure and pore pressure in increments of 500 psi. The dead crude oil was routed from the automatic valve 255 to the valve 416 and to the second core holder 104, as shown by connection block B in FIGS. 2A and FIG. 4A. The dead crude oil was routed from the low permeable core plug via the outlet of the second core holder 104 to the second oil/water separation system 124 via the valves 906 and 908 and then to the second back pressure regulator 1002 via the automatic valve 1010 and the automatic valve 1016 shown in FIG. 10 to first establish a pore pressure of 500 psi. During the process of establishing the confining pressure and pore pressure for the second core holder 104, the valves 420, 422, 456, and 458 shown in FIG. 4A were all open and the automatic valves 906, 908, and 918 shown in FIG. 9 were all open.

The dual core flooding apparatus 100 may be used to evaluate the wettability of the core plug, as the wettability of the core plug is a factor in influencing oil recovery by water, CO2, and chemical flooding process. The restoration of wettability of the core plug is used to restore the wettability at reservoir conditions for oil recovery studies. An example experiment of the restoration of wettability of a core plug using the dual core flooding apparatus 100 is described infra.

The temperature of the second oven 134 was set to 102° C. and allowed to stabilize overnight to reach temperature equilibrium. The heating of the components inside the second oven 134 may result in the expansion of the dead crude oil in the high permeable core plug (HPCP) and the low permeable core plug (LPCP). Constant pore pressures may be maintained by the back pressure regulation systems 120 and 126, and a constant confining pressure may be maintained by the automated confining pressure system 114.

Dead crude oil in the high permeable core plug (HPCP) and the low permeable core plug (LPCP) may be displaced using live oil in the amount of about 4 pore volume for each core plug and at a flow rate of about 1.00 cc/min and an injection pressure greater than 3200 psi. The live oil was injected using the fluids delivery system 106 shown in FIG. 2A and the second pump 207 and fluid accumulator 201. The live oil was injected into the high permeable core plug in the first core holder 102 via the second pump 207 and fluid accumulator 201 and by routing via the following components shown in FIG. 2A: the second pump 207, the valve 211, the automatic valve 230, the valve 233, the fluid accumulator 201, the valve 245, the automatic valve 248, the valve 250, the automatic valve 252 and the automatic valve 254 (with the automatic valve 255 being closed). The live oil was routed to through the image capture system 112 shown in FIG. 3 via the valve 300 and the valve 316. The live oil was then routed to the high permeable core plug via the inlet of the first core holder 102 shown in FIG. 4A via the automatic valve 320 and the valve 410. The live oil was routed from the high permeable core plug via the outlet of the first core holder shown in FIG. 4A via the valve 460 and the automatic valve 466 to the density and viscosity measurement system 116. The live oil was routed to bypass the density meter 700 and the viscosity meter 702 via the valve 468, the automatic valve 728 and the automatic valve 726, shown in FIG. 7. The live oil was then routed to the first back pressure regulator 1000 via the valve 1006 shown in FIG. 10. During the injection of live oil into the high permeable core plug in the first core holder 102, the valves 412, 414, 452, and 454 were closed, as shown in FIG. 4C.

The live oil may be injected into the low permeable core plug in the second core holder 104 at a flow rate of 1.0 cc/min and an injection pressure greater than 3200 psi using the second pump 207 and the fluid accumulator 201 of the fluids delivery system 106 and the same routing path described supra to the automatic valves 254 and 255. The live oil was routed from the automatic valve 255 (with the automatic valve 254 closed) to the valve 416 and to the second core holder 104. The live oil was routed from the outlet of the second core holder 104 to the second oil/water separation system 124 via the automatic valves 906 and 908, the automatic valve 918, and then to the second back pressure regulator 1002 via the automatic valve 1010, the valve 1012, and the automatic valve 1016 shown in FIG. 10. During the injection of live oil into the high permeable core plug in the first core holder 102, the valves 420, 422, 456, and 458 were closed.

The high permeable core plug and the low permeable core plug were aged about three weeks in dead crude oil at ambient conditions and about three weeks in the live crude oil at reservoir conditions of a pore pressure of about 3200 psi and a temperature of about 102° C. to restore the wettability of the core plugs. During the aging process, about one pore volume of live crude oil was injected each day to monitor injection pressure and water production for correction of initial water and original oil saturation. At the end of the aging process, differential pressure across the core plugs and injection flow rates were recorded to determine the effective oil permeability ($K_{eo}$). In this experiment of aging the core plugs with dead crude oil and live crude oil, the high permeable core plug and the low permeable core plug have a mixed wettability system (that is, slightly oil-wet).

The dual core flooding apparatus 100 may be also be used to perform seawater flooding experiments to determine oil recovery factor, remaining oil saturation, and the performance of seawater flooding for both the high permeable core plug and the low permeable core plug. The seawater flooding test was conducted at reservoir conditions, a pore pressure of 3200 psi, a confining pressure of 4500 psi, and a temperature of 102° C. The seawater injection flow rate was about 0.5 cc/min. Before running the seawater flooding test, the live crude oil in the inlet lines, bypass lines, and outlet lines of the core holders 102 and 104 was cleaned out using injection seawater and the valves 412, 414, 452, and 454 for the first core holder 102 and the valves 420, 422, 456, and 458 for the core holder 104.

Seawater was injected simultaneously to both the high permeable core plug in the first core holder 102 and the low permeable core plug in the second core holder 104 using the first pump 206 and the fluid accumulator 204 of the fluids delivery system 106. The seawater was injected into the high permeable core plug in the first core holder 102 and the low permeable core plug in the second core holder 104 by routing the seawater via the following components shown in FIG. 2A: the first pump 206, the valve 208, the automatic valve 212, the connector 216, the automatic valve 220, the valve 227, the fluid accumulator 204, the valve 240, the connector 236, the valve 253, and the automatic valve 254 open to the high permeable core plug in the first core holder 102 and the automatic valve 255 open to the low permeable core plug in the second core holder 104. The seawater was routed to bypass the image capture system 112 shown in FIG. 3 via the valve 302 and the valve 318 (and by closing the valves 300 and 316). The seawater was then routed to the high permeable core plug via the inlet of the first core holder 102 shown in FIG. 4A via the automatic valve 320 and the valve 410. The seawater was routed from the high permeable core plug via the outlet of the first core holder 102 shown in FIG. 4A via the valve 460 and the automatic valve 468 to the bypass of the density and viscosity measurement system 116. The seawater was routed to bypass the density meter 700 and the viscosity meter 702 via the automatic valve 468 and the automatic valve 730 shown in FIG. 7. The seawater was then routed to the first oil/water separation system 118 via the valve 806 and into the separator 800, where the amount of produced oil was measured. The seawater was routed from the outlet of the separator 800 via the automatic valve 816 and the automatic valve 1008 to the back pressure regulator 1000 shown in FIG. 10, where the seawater was routed to the first effluent measurement system 122 and the seawater production was measured using the balance 1206 of the first effluent measurement system 122.

The seawater was routed from the fluids delivery system 106 to the low permeable core plug in the second core holder 104 via the valve 255, as shown in FIG. 2. The seawater was then routed via the valve 416 shown in FIG. 4C to the low permeable core plug via the inlet of the second core holder 104. The produced oil and seawater were routed from the low permeable core plug via the outlet of the second core holder 104 shown in FIG. 4A to the second oil/water separation system 124 via the automatic valve 906 and into the separator 900 shown in FIG. 9, where the amount of produced oil was measured. The seawater was routed from the outlet of the separator 900 via the automatic valve 916 and the automatic valves 1010 and 1016 to the back pressure regulator 1002 shown in FIG. 10, where the seawater was routed to the second effluent measurement system 128 and the seawater production was measured using the balance 1306 of the first effluent measurement system 128. The seawater flooding test was finished when the water cut from either the high permeable core plug in the first core holder 102 or the low permeable core plug in the second core holder 104 reached 99%, at which point the first pump 206 of the fluids delivery system 106 was stopped and the automatic valve 253 was closed.

In some embodiments, supercritical CO2 may be injected after seawater flooding to recover remaining oil. The dual core flooding apparatus 100 may be also be used to perform CO2 flooding experiments after seawater flooding experiments. A supercritical CO2 flooding experiment was conducted by simultaneously injecting supercritical CO2, as a displacing agent, into the high permeable core plug in the first core holder 102 and the low permeable core plug in the second core holder 104 and followed by water injection. The supercritical CO2 flooding test was conducted at reservoir conditions of a pore pressure of about 3200 psi and a temperature of about 102°. The supercritical CO2 injection was injected simultaneously to both the high permeable core plug in the first core holder 102 and the low permeable core plug in the second core holder 104 using the second pump 207 and the fluid accumulator 202 of the fluids delivery system 106. The second pump 207 was started in a mode of pair constant pressure to establish the pump pressure the same as the pore pressure of the core plugs in the core holders 102 and 104. The supercritical CO2 was routed via the valve 211, the automatic valve 231, the valve 235, the fluid accumulator 202, the valve 246, the automatic valve 249, the valve 250, and the automatic valve 252. When the pressure on both sides of the automatic valve 252 reached the same pressure, the second pump 207 was stopped and the pump changed to pair constant flow rate at the desired CO2 injection rate. The second pump 207 was restarted and the automatic valve 252 was opened, and the supercritical CO2 was routed via the automatic valve 254 open to the high permeable core plug in the first core holder 102 and the automatic valve 255 open to the low permeable core plug in the second core holder 104. The supercritical CO2 was routed to bypass the image capture system 112 shown in FIG. 3 via the valve 302 and the valve 318 (and by closing the valves 300 and 316). The supercritical $CO_2$ was then routed to the inlet of the first core holder 102 shown in FIG. 4A via the automatic valve 320 and the valve 410. The supercritical $CO_2$ was routed via the valve 416 to the inlet of the second core holder 104.

The produced oil, water, and CO2 were routed from the high permeable core plug via the outlet of the first core holder 102 and low permeable core plug via the outlet of the second core holder 104 in the same route described supra for the produced oil, supercritical $CO_2$, and seawater to first oil/water separation system 118 and the second oil water separation system 124 and then to the respective back pressure regulators 1000 and 1002. One pore volume of supercritical CO2 was injected simultaneously into the high permeable core plug in the first core holder 102 and the low permeable core plug in the second core holder 104 at an expectant injection rate. During the supercritical CO2 miscible flooding, the upstream pressure and the differential pressure across the high permeable core plug and the low permeable core plug were measured using the differential pressure measurement systems 108 and 110 and used to evaluate the recovery performance, determine effective or relative permeability, and injectivity to supercritical CO2 at the remaining oil saturation (ROS) after the supercritical CO2 flooding. Additionally, the amount of oil may be measured by a gradate tube at ambient conditions.

The direct injection of supercritical CO2 to displace crude oil may cause viscous fingering and supercritical CO2 override, and the unfavorable viscosity ratio between crude oil and supercritical CO2 may cause inefficient displacement during supercritical CO2 flooding. Thermal foam slug injection (TFSI) may be used to improve areal and vertical sweet efficiencies by plugging high permeable zones and stabilizing viscous fingering. The dual core flooding apparatus 100 may be used to perform thermal foam slug injection experiments on core plugs in the first core holder 102 and second core holder 104. A thermal foam slug injection test was conducted after the supercritical CO2 flooding experiment described supra. After the supercritical CO2 injection, the automatic valves 254, 255, 252, and valves 250, 249, and 246 were closed and the fluid accumulator 202 was replaced with an external accumulator having a thermal foam solution. The bottom valve of the external accumulator was connected to the valve 235 and the top valve of the external accumulator was connected to the valve 246. Before injection of the thermal foam solution into the high permeable core plug in the first core holder 102, the solution was evaluated using the image capture system 112 and the density and viscosity were measured using the density and viscosity measurement system 116. During such evaluation and measurement, the first core holder 102 and first oil/water separation system 118 were bypassed, as shown in FIG. 14, and the thermal foam solution was routed to the back pressure regulator 1000 shown in FIG. 10. The low permeable core plug was isolated or open during the test.

The thermal foam solution was injected according to the following procedure. The valves 428 and 430 connecting the first differential pressure measurement system 108 were closed and the bypass valves 412, 414, and 454 were opened, as shown in FIG. 4. To build pressure in the thermal foam solution accumulator, the second pump 207 was set and started in a mode of pair constant pressure and the valves 211, 231 and 235 to the external accumulator were opened, as shown in FIG. 2. The thermal solution was routed via the valve 246, the automatic valve 249, the valve 250, to the automatic valve 252. When the pressure on both sides of the automatic valve 252 was the same pressure, the second pump 207 was stopped and restarted in a mode of pair constant flow rate to establish an expectant injection flow rate of the thermal foam solution. The automatic valve 252 was opened, the automatic valve 254 to the high permeable core plug in the first core holder 102 was opened, and the automatic valve 255 to the low permeable core plug in the second core holder 104 was closed. The thermal foam solution was routed through the image capture system 112 via the valve 300, the viewing cell 308, and the valve 316. The thermal foam solution was then routed from the image capture system 112 via the automatic valve 320 and through a bypass of the first core holder 102 via the valve 414 and the valve 454. The thermal foam solution was then routed to the density and viscosity measurement system 116 via the valve 460 and the automatic valve 466 where the density and viscosity were measured. After evaluation and measurement of the thermal foam solution, the thermal foam solution was injected into the high permeable core plug in the first core holder 102 by closing the bypass valves 412, 414, and 454 and routing the thermal foam solution to the high permeable core plug via the inlet of the first core holder 102 via the valves 320 and 410 shown in FIG. 4A. The volume of slug injection of the thermal foam solution as a percentage of pore volume of the high permeable core and the pressure build up during injection were recorded as a function of time.

The dual core flooding apparatus 100 may be used to perform post-CO2 or post-seawater flooding on core plugs in the first core holder 102 and second core holder 104. A post-CO2 was conducted after the thermal foam solution experiment. The external accumulator with the thermal foam solution was replaced by accumulator 202 and the valves 302 and 318 of the image capture system 112 and the bypass valves 414 and 454 of the first core holder 102 were opened and the thermal foam solution was flushed by routing CO2 to the first back pressure regulator 1000. After flushing the thermal foam solution, the valves 414 and 454 of the first core holder 102 were closed and the automatic valves 320 and 410 to the first core holder and the automatic valve 255 and the valve 416 to the second core holder 104 were opened. The post-CO2 injection procedure was the same as the initial CO2 injection procedure described supra, and both the high permeable core plug in first core holder 102 and the low permeable core plug in the second core holder 104 were injected. The post-CO2 injection procedure was stopped when no more oil was produced from the high permeable core plug and the low permeable core plug. The second pump 207 was stopped and the automatic valves 254 and 255 shown in FIG. 2 were closed. During the post-CO2 injection experiment, the amount of oil production from and the differential pressure across the high permeable core plug and the low permeable core plug were recorded as a function of time.

After the completion of the post-CO2 injection, the dual core flooding apparatus 100 was shut down by decreasing the temperature of the ovens 132 and 134 to ambient temperature and removing the core plugs from the first core holder 102 and the second core holder 104. Before removing the core plugs, all bypass valves for the image capture system 112, the core holders 102 and 104, the density and viscosity measurement system 116, and the oil/water separators 118 and 124 were opened. The pore pressure was reduced by starting the first pump 206, the second pump 207 or both in a pair constant pressure mode or by using the back pressure regulation systems 120 and 126. The confining pressure was reduced by suing the automating confining pressure system 114. Both the pore pressure and the confining pressure were reduced in 500 psi increments until zero pressure was achieved for the pore pressure and confining pressure. Next, all inlet lines, outlet lines, bypass lines, and lines for the differential pressure measurement systems 108 and 110 connected to the core holders 102 and 104 were disconnected. The end caps of the core holders 102 and 104 were removed and the fluid distribution plugs for both ends in the core holders 102 and 104 were removed. The core plugs were then taken out and a Dean Stark extraction was conducted to determine residue oil saturation ($S_{or}$).

Ranges may be expressed in the disclosure as from about one particular value, to about another particular value, or both. When such a range is expressed, it is to be understood that another embodiment is from the one particular value, to the other particular value, or both, along with all combinations within said range.

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the embodiments described in the disclosure. It is to be understood that the forms shown and described in the disclosure are to be taken as examples of embodiments. Elements and materials may be substituted for those illustrated and described in the disclosure, parts and processes may be reversed or omitted, and certain features may be utilized independently, all as would be apparent to one skilled in the art after having the benefit of this description. Changes may be made in the elements described in the disclosure without departing from the spirit and scope of the disclosure as described in the following claims. Headings used in the disclosure are for organizational purposes only and are not meant to be used to limit the scope of the description.

What is claimed is:

1. A dual core flooding apparatus for analyzing a plurality of core plugs, the apparatus comprising:
    a first core holder and a second core holder, each core holder being operable to contain at least one core plug of the plurality of core plugs, each core holder further comprising:
        an inlet port operable to receive at least one fluid into the core holder and into contact with the core plug; and
        an outlet port operable for removal of the at least one fluid from the core holder;
    a fluids delivery system in fluid communication with the inlet port, the fluids delivery system operable to introduce the at least one fluid into at least one core holder through the inlet port;
    a first separator operable to separate hydrocarbon fluid from the at least one fluid, the first separator in fluid communication with the outlet port of the first core holder;
    a second separator operable to separate hydrocarbon fluid from the at least one fluid, the second separator in fluid communication with the outlet port of the second core holder;
    a pressure confining system operable to maintain a first confining pressure in the first core holder and a second confining pressure in the second core holder;
    a first back pressure control system configured to maintain pore pressure within the core plug contained in the first core holder independent of a pore pressure associated with the second core holder, the first separator in fluid communication with the first back pressure control system;
    a second back pressure control system configured to maintain pore pressure within the core plug contained in the second core holder independent of the pore pressure associated with the first core holder;
    a data acquisition system configured to acquire properties of the at least one fluid exiting from the outlet port of the first core holder or the outlet port of the second core holder; and
    a density meter coupled to the outlet port of the first core holder and the output port of the second core holder, wherein the density meter is configured to measure a density of the at least one fluid exiting from the outlet port of the first core holder or the outlet port of the second core holder;
    a viscosity meter coupled to the outlet port of the first core holder and the output port of the second core holder, wherein the viscosity meter is configured to measure a viscosity of the at least one fluid exiting from the outlet port of the first core holder or the outlet port of the second core holder; and
    an image capture apparatus, the image capture apparatus comprising:
        a viewing cell coupled to the fluids delivery system via at least one valve; and
        a camera configured to capture images of the at least one fluid before the at least one fluid is received by the first core holder.

2. The dual core flooding apparatus of claim 1, the image capture apparatus comprising a pump operable to maintain a confining pressure in the viewing cell.

3. The dual flooding apparatus of claim 1, wherein the fluids delivery system comprises:
    at least one fluid accumulator; and
    at least one pump coupled to the at least one fluid accumulator via at least one valve.

4. The dual flooding apparatus of claim 3, wherein the at least one fluid accumulator comprise a first fluid accumulator coupled to the inlet port of the first core holder via a first at least one valve and a second fluid accumulator coupled to the inlet port of the second core holder via a second at least one valve.

5. The dual core flooding apparatus of claim 1, wherein the fluids delivery system comprises:
    a plurality of valves arranged to define a first fluid flow path from a first fluid accumulator to the inlet port of the first core holder and a second fluid flow path from a second fluid accumulator to the inlet port of the second core holder when a first group of the plurality of valves are open and a second group of the plurality of valves are closed.

6. The dual core flooding apparatus of claim 5, wherein the plurality of valves are further arranged to define a third fluid flow path from the first fluid accumulator to the inlet port of the first core holder and a fourth fluid flow path from the first fluid accumulator to the inlet port of the second core holder when a third group of the plurality of valves are open and a fourth group of the plurality of valves are closed.

7. The dual core flooding apparatus of claim 1, comprising:
   a first differential pressure measurement apparatus configured to measure differential pressure across the first core holder and provide a first differential pressure measurement to the data acquisition system; and
   a second differential pressure measurement apparatus configured to measure differential pressure across the second core holder and provide a second differential pressure measurement to the data acquisition system.

8. The dual core flooding apparatus of claim 1, comprising:
   a first effluent measurement system coupled to the first back pressure regulation system, the first effluent measurement system comprising a first fraction collector configured to measure an amount of liquid effluent produced from the first back pressure system; and
   a second effluent measurement system coupled to the second back pressure regulation system, the second effluent measurement system comprising a second fraction collector configured to measure an amount of liquid effluent produced from the second back pressure system.

9. The dual core flooding apparatus of claim 1, wherein the at least one fluid comprises live crude oil, dead crude oil, or seawater.

10. The dual core flooding apparatus of claim 1, wherein the properties comprise at least one of a density, a viscosity, an amount of hydrocarbon fluid, and an amount of water.

11. The dual core flooding apparatus of claim 1, wherein the data acquisition system is configured to acquire a first differential pressure across the first core holder and a second differential pressure across the second core holder.

12. A dual core flooding apparatus for analyzing a plurality of core plugs, the apparatus comprising: a first core holder comprising a first core plug, the first core holder rotationally mounted on a fixture and configured to rotate between a vertical orientation and a horizontal orientation; a second core holder comprising a second core plug, the second core holder rotationally mounted on the fixture and configured to rotate between a vertical orientation and a horizontal orientation; a fluids delivery system configured to introduce a first fluid into the first core plug and introduce a second fluid into the second core plug; a first back pressure regulation system in fluid communication with the first core holder and operable to maintain a first pore pressure of the first core plug; a second back pressure regulation system in fluid communication with the second core holder and operable to maintain a second pore pressure of the second core plug, the second pore pressure maintained independently of the first pore pressure; a pressure confining system in fluid communication with the first core holder and the second core holder and operable to maintain a first confining pressure in the first core holder and a second confining pressure in the second core holder; an image capture system positioned between the fluids delivery system and the first core holder, wherein the image capture system comprises a camera configured to capture images of the first fluid before introduction of the first fluid into the first core holder.

13. The dual core flooding apparatus of claim 12, comprising a data acquisition system configured to obtain properties of the first fluid after the first fluid exits the first core holder.

14. The dual core flooding apparatus of claim 13, wherein the properties comprise at least one of a density, a viscosity, an amount of hydrocarbon fluid, and an amount of water.

15. The dual core flooding apparatus of claim 13, wherein the data acquisition system is further configured to obtain properties of the second fluid after the second fluid exits the second core holder.

16. The dual core flooding apparatus of claim 12, wherein the first fluid comprises live crude oil, dead crude oil, seawater or carbon dioxide and the second fluid comprise live crude oil, dead crude oil, seawater or carbon dioxide.

* * * * *